(12) United States Patent
Wright et al.

(10) Patent No.: US 8,016,792 B2
(45) Date of Patent: Sep. 13, 2011

(54) UNIVERSAL CATHETER SECUREMENT DEVICE

(75) Inventors: Clifford A. Wright, San Diego, CA (US); Robert F. Eisele, Carlsbad, CA (US); Thomas R. Jackson, La Jolla, CA (US)

(73) Assignee: Venetec International, Inc., Covington, GA (US)

( * ) Notice: Subject to any disclaimer, the term of this patent is extended or adjusted under 35 U.S.C. 154(b) by 1149 days.

(21) Appl. No.: 11/622,408

(22) Filed: Jan. 11, 2007

(65) Prior Publication Data

US 2007/0219500 A1 Sep. 20, 2007
US 2009/0024090 A2 Jan. 22, 2009

Related U.S. Application Data

(60) Provisional application No. 60/758,386, filed on Jan. 12, 2006, provisional application No. 60/865,095, filed on Nov. 9, 2006.

(51) Int. Cl.
*A61M 5/32* (2006.01)
(52) U.S. Cl. .................. 604/174; 604/180; 604/178
(58) Field of Classification Search .................. 604/211, 604/232, 218, 131, 197, 174, 180, 178; 128/DIG. 26, DIG. 6
See application file for complete search history.

(56) References Cited

U.S. PATENT DOCUMENTS

| | | |
|---|---|---|
| 2,525,398 A | 10/1950 | Collins |
| 2,533,961 A | 12/1950 | Rouseau et al. |
| 2,707,953 A | 5/1955 | Ryan |
| 3,059,645 A | 10/1962 | Hasbrouck et al. |
| 3,064,648 A | 11/1962 | Bujan |
| 3,167,072 A | 1/1965 | Stone et al. |
| 3,482,569 A | 12/1969 | Raffaelli |
| 3,529,597 A | 9/1970 | Fuzak |
| 3,602,227 A | 8/1971 | Andrew |
| 3,630,195 A | 12/1971 | Santomieri |

(Continued)

FOREIGN PATENT DOCUMENTS

CA 995 995 8/1976

(Continued)

OTHER PUBLICATIONS

International Search Report & Written Opinion, Application No. PCT/US07/84346, dated Oct. 31, 2008, 8 pgs.

(Continued)

*Primary Examiner* — Theodore Stigell
*Assistant Examiner* — Bradley Thomas, Jr.
(74) *Attorney, Agent, or Firm* — Knobbe Martens Olson & Bear LLP

(57) ABSTRACT

A universal securing device for holding catheters of various shapes and sizes and the like in place includes a base and cover. The cover may be connected to the base by a hinge which allows the cover to be lifted open or pushed down into a closed position, over a catheter fitting. The base may have locating elements configured and arranged to fit around catheter fittings of various sizes, and the locating elements prevent substantial movement of a catheter fitting and catheter in various dimensions. The cover may include capture elements which act to grip and compress the catheter fitting when the securing device is in a closed position, thus preventing substantial movement of a catheter fitting and catheter in various dimensions. The base may be attached to a patient with an adhesive pad attached to the bottom surface of the base.

26 Claims, 29 Drawing Sheets

U.S. PATENT DOCUMENTS

| | | | |
|---|---|---|---|
| 3,677,250 A | 7/1972 | Thomas |
| 3,766,915 A | 10/1973 | Rychlik |
| 3,834,380 A | 9/1974 | Boyd |
| 3,847,370 A | 11/1974 | Engelsher |
| 3,856,020 A | 12/1974 | Kovac |
| 3,896,527 A | 7/1975 | Miller et al. |
| 3,900,026 A | 8/1975 | Wagner |
| 3,906,946 A | 9/1975 | Nordstrom |
| 3,942,228 A | 3/1976 | Buckman et al. |
| 3,973,565 A | 8/1976 | Steer |
| 4,020,835 A | 5/1977 | Nordstrom et al. |
| 4,057,066 A | 11/1977 | Taylor |
| 4,059,105 A | 11/1977 | Cutruzzula et al. |
| 4,082,094 A | 4/1978 | Dailey |
| 4,114,618 A | 9/1978 | Vargas |
| 4,129,128 A | 12/1978 | McFarlane |
| 4,133,307 A | 1/1979 | Ness |
| 4,142,527 A | 3/1979 | Garcia |
| 4,161,177 A | 7/1979 | Fuchs |
| 4,193,174 A | 3/1980 | Stephens |
| 4,224,937 A | 9/1980 | Gordon |
| 4,248,229 A | 2/1981 | Miller |
| 4,250,880 A | 2/1981 | Gordon |
| 4,316,461 A | 2/1982 | Marais et al. |
| 4,324,236 A | 4/1982 | Gordon et al. |
| 4,326,519 A | 4/1982 | D'Alo et al. |
| 4,333,468 A | 6/1982 | Geist |
| 4,362,156 A | 12/1982 | Feller, Jr. et al. |
| 4,392,853 A | 7/1983 | Muto |
| 4,397,647 A | 8/1983 | Gordon |
| 4,449,975 A | 5/1984 | Perry |
| 4,453,933 A | 6/1984 | Speaker |
| 4,474,559 A | 10/1984 | Steiger |
| 4,480,639 A | 11/1984 | Peterson et al. |
| 4,516,968 A | 5/1985 | Marshall et al. |
| 4,517,971 A | 5/1985 | Sorbonne |
| 4,563,177 A | 1/1986 | Kamen |
| 4,633,863 A | 1/1987 | Filips et al. |
| 4,650,473 A | 3/1987 | Bartholomew et al. |
| 4,660,555 A | 4/1987 | Payton |
| 4,711,636 A | 12/1987 | Bierman |
| 4,742,824 A | 5/1988 | Payton et al. |
| 4,762,513 A | 8/1988 | Choy et al. |
| 4,808,162 A | 2/1989 | Oliver |
| 4,823,789 A | 4/1989 | Beisang, III |
| 4,826,466 A | 5/1989 | Triquet |
| 4,852,844 A | 8/1989 | Villaveces |
| 4,857,058 A | 8/1989 | Payton |
| 4,863,432 A | 9/1989 | Kvalo |
| 4,869,465 A | 9/1989 | Yirmiyahu et al. |
| 4,880,412 A | 11/1989 | Weiss |
| 4,896,465 A | 1/1990 | Rhodes et al. |
| 4,897,082 A | 1/1990 | Erskine |
| 4,898,587 A | 2/1990 | Mera |
| 4,919,654 A | 4/1990 | Kalt |
| 4,932,943 A | 6/1990 | Nowak |
| 4,944,728 A | 7/1990 | Carrell et al. |
| 4,952,207 A | 8/1990 | Lemieux |
| 4,955,864 A | 9/1990 | Hajduch |
| 4,976,700 A | 12/1990 | Tollini |
| 4,997,421 A | 3/1991 | Palsrok et al. |
| 5,000,741 A | 3/1991 | Kalt |
| 5,037,397 A | 8/1991 | Kalt et al. |
| 5,073,166 A | 12/1991 | Parks et al. |
| 5,073,170 A | 12/1991 | Schneider |
| 5,084,026 A | 1/1992 | Shapiro |
| 5,098,399 A | 3/1992 | Tollini |
| 5,112,313 A | 5/1992 | Sallee |
| 5,137,519 A | 8/1992 | Littrell et al. |
| 5,147,322 A | 9/1992 | Bowen et al. |
| 5,156,641 A | 10/1992 | White |
| 5,192,273 A | 3/1993 | Bierman et al. |
| 5,192,274 A | 3/1993 | Bierman |
| 5,195,981 A | 3/1993 | Johnson |
| 5,226,892 A | 7/1993 | Boswell |
| 5,266,401 A | 11/1993 | Tollini |
| 5,267,967 A | 12/1993 | Schneider |
| 5,282,463 A | 2/1994 | Hammersley |
| 5,292,312 A | 3/1994 | Delk et al. |
| 5,304,146 A | 4/1994 | Johnson et al. |
| 5,306,243 A | 4/1994 | Bonaldo |
| 5,314,411 A | 5/1994 | Bierman |
| 5,322,514 A | 6/1994 | Steube et al. |
| 5,330,438 A | 7/1994 | Gollobin et al. |
| 5,338,308 A | 8/1994 | Wilk |
| 5,342,317 A | 8/1994 | Claywell |
| 5,344,406 A | 9/1994 | Spooner |
| 5,344,414 A | 9/1994 | Lopez et al. |
| 5,346,479 A | 9/1994 | Schneider |
| 5,352,211 A | 10/1994 | Merskelly |
| 5,354,282 A | 10/1994 | Bierman |
| 5,354,283 A | 10/1994 | Bark et al. |
| 5,380,293 A | 1/1995 | Grant |
| 5,380,294 A | 1/1995 | Persson |
| 5,380,301 A | 1/1995 | Prichard et al. |
| 5,382,239 A | 1/1995 | Orr et al. |
| 5,382,240 A | 1/1995 | Lam |
| 5,389,082 A | 2/1995 | Baugues et al. |
| 5,395,344 A | 3/1995 | Beisang, III et al. |
| 5,403,285 A | 4/1995 | Roberts |
| 5,413,562 A | 5/1995 | Swauger |
| 5,443,460 A | 8/1995 | Milusek |
| 5,449,349 A | 9/1995 | Sallee et al. |
| 5,456,671 A | 10/1995 | Bierman |
| 5,468,228 A | 11/1995 | Gebert |
| 5,468,230 A | 11/1995 | Corn |
| 5,468,231 A | 11/1995 | Newman et al. |
| 5,470,321 A | 11/1995 | Forster et al. |
| D364,922 S | 12/1995 | Bierman |
| 5,147,322 A | 1/1996 | Bowen et al. |
| 5,484,420 A | 1/1996 | Russo |
| 5,496,282 A | 3/1996 | Militzer et al. |
| 5,496,283 A | 3/1996 | Alexander |
| 5,499,976 A | 3/1996 | Dalton |
| 5,520,656 A | 5/1996 | Byrd |
| 5,522,803 A | 6/1996 | Teissen-Simony |
| 5,527,293 A | 6/1996 | Zamierowski |
| 5,549,567 A | 8/1996 | Wolman |
| D375,355 S | 11/1996 | Bierman |
| 5,638,814 A | 6/1997 | Byrd |
| 5,697,907 A | 12/1997 | Gaba |
| 5,738,660 A | 4/1998 | Luther |
| 5,795,335 A | 8/1998 | Zinreich |
| 5,800,402 A | 9/1998 | Bierman |
| 5,827,230 A | 10/1998 | Bierman |
| 6,001,081 A | 12/1999 | Collen |
| 6,027,480 A | 2/2000 | Davis et al. |
| 6,213,979 B1 * | 4/2001 | Bierman ..................... 604/174 |
| 6,290,676 B1 | 9/2001 | Bierman |
| 6,332,874 B1 | 12/2001 | Eliasen et al. |
| 6,447,485 B2 | 9/2002 | Bierman |
| 6,488,664 B1 | 12/2002 | Solomon et al. |
| 6,491,713 B1 | 12/2002 | Deininger et al. |
| 6,572,588 B1 | 6/2003 | Bierman et al. |
| 6,582,403 B1 | 6/2003 | Bierman et al. |
| 6,585,703 B1 | 7/2003 | Kassel et al. |
| 6,663,600 B2 | 12/2003 | Bierman |
| 6,786,892 B2 | 9/2004 | Bierman |
| 6,837,875 B1 | 1/2005 | Bierman |
| 6,872,194 B2 | 3/2005 | Doyle et al. |
| 6,929,625 B2 | 8/2005 | Bierman |
| 6,951,550 B2 | 10/2005 | Bierman |
| 6,972,003 B2 | 12/2005 | Bierman et al. |
| 6,979,320 B2 | 12/2005 | Bierman |
| 6,984,145 B1 | 1/2006 | Lim et al. |
| 7,247,150 B2 | 7/2007 | Bierman |
| D593,680 S | 6/2009 | Hafele et al. |
| 2002/0068904 A1 * | 6/2002 | Bierman et al. ............. 604/180 |
| 2004/0034330 A1 * | 2/2004 | Bierman et al. ............. 604/500 |
| 2005/0113759 A1 | 5/2005 | Mueller, Jr. et al. |
| 2005/0192539 A1 | 9/2005 | Bierman |
| 2006/0089600 A1 | 4/2006 | Bierman et al. |
| 2007/0219500 A1 | 9/2007 | Wright et al. |

FOREIGN PATENT DOCUMENTS

| | | |
|---|---|---|
| CA | 2 281 457 | 2/2001 |
| DE | 2341297 | 4/1975 |

| | | |
|---|---|---|
| EP | 0064284 A2 | 4/1982 |
| EP | 0247590 A2 | 12/1987 |
| EP | 356683 A | 7/1989 |
| FR | 1184139 | 7/1959 |
| FR | 2381529 | 9/1978 |
| FR | 2852520 | 9/2004 |
| GB | 2063679 | 6/1981 |
| GB | 2086466 A | 5/1982 |
| GB | 2344054 | 5/2000 |
| JP | 63-211700 | 9/1988 |
| JP | 1992-51767 | 4/1992 |
| JP | 1994-344852 | 12/1994 |
| JP | 1995-28563 | 5/1995 |
| WO | WO 80/01458 | 7/1980 |
| WO | WO 85/02774 | 7/1985 |
| WO | WO 91/16939 | 11/1991 |
| WO | WO 92/19309 | 11/1992 |
| WO | WO 96/10435 | 4/1996 |
| WO | WO 98/53872 | 12/1998 |
| WO | WO 99/02399 | 1/1999 |

OTHER PUBLICATIONS

Multiple-Lumen Central Venous Catheterization Product With ARROW+gard™ Antiseptic Surface (Arrow International brochure) (Apr. 1994).

Photographs (4) of Catheter Clamp and Rigid Fastener sold by Arrow International. Inc.

US Patent and Trademark Office, Combined International Search Report and Written Opinion of the International Searching Authority, dated Sep. 25, 2007.

* cited by examiner

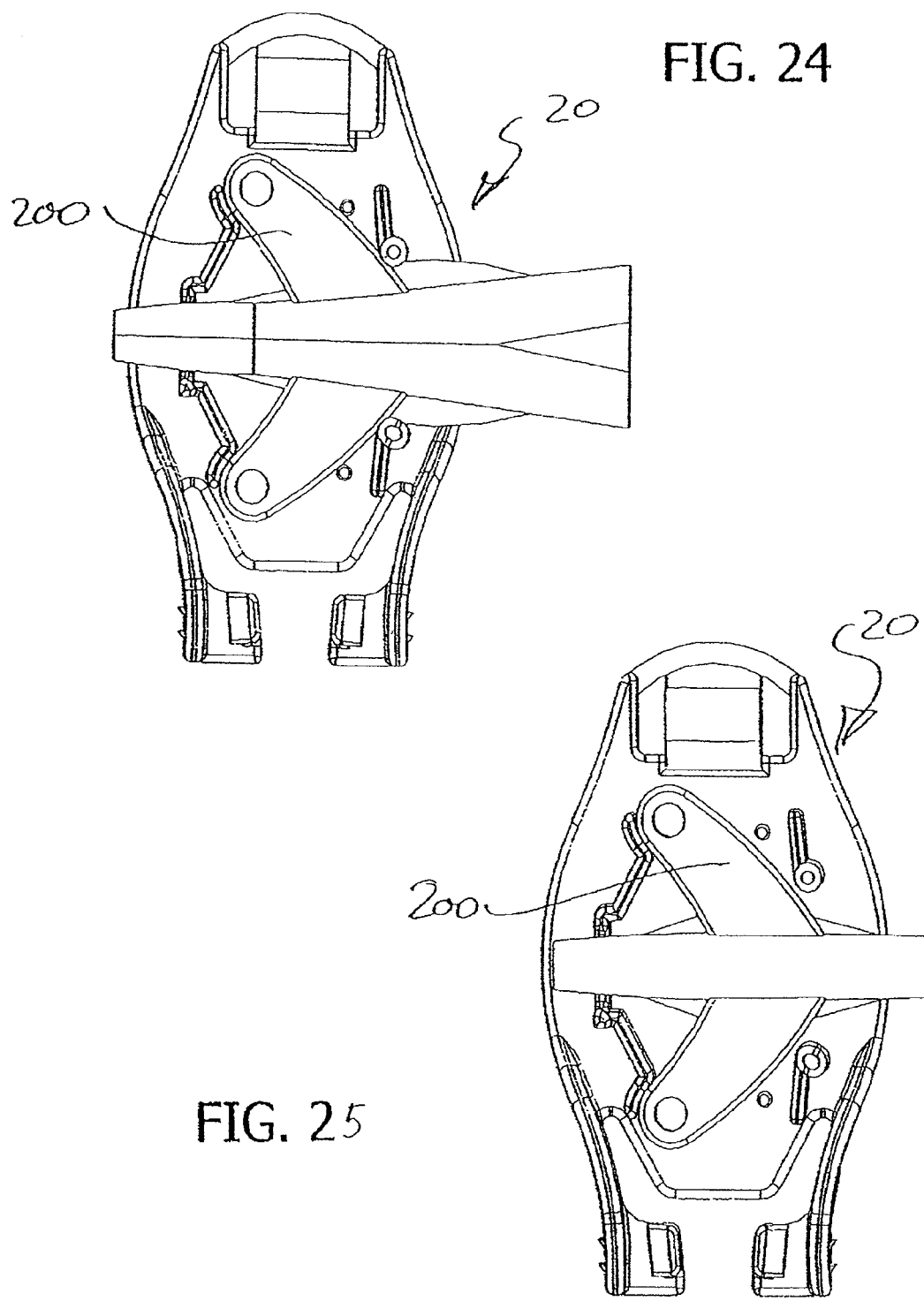

UNIVERSAL CATHETER SECUREMENT DEVICE

CROSS-REFERENCE TO RELATED APPLICATIONS

This application claims the benefit of U.S. Provisional Patent Application No. 60/758,386, filed Jan. 12, 2006, and U.S. Provisional Patent Application No. 60/865,095, filed Nov. 9, 2006. Both of these applications are incorporated herein by reference.

BACKGROUND

The invention relates to a system for securing a medical device in place on a patient. Typically, the invention may be used for securing a catheter, tube or other elongated medical device to a patient.

It is often necessary to introduce fluids and liquid medications directly into a blood vessel of a patient. A simple intravenous (IV) line is usually acceptable for short term general use. IV lines are typically placed onto a patient's arm and secured with tape. For longer term and more specialized needs, catheters or other devices are used. A catheter is essentially a tube inserted through an incision in the skin into a blood vessel in the patient's body, generally without surgery. Peripherally inserted central catheters (PICCs) are frequently used to provide medications or fluids to home care patients over longer periods of time. PICCs may also be used for frequent blood sampling.

A PICC line and similar catheters may remain in place in a patient for several weeks or months. It is important that movement of the catheter be minimized. If the catheter is not secured in place, it may be inadvertently displaced from the intended location. Consequently, medication delivered through the PICC line may then be released at an incorrect position within the blood vessel. Repeated back and forth catheter movement, or positioning, can cause irritation of the blood vessel, disrupt proper introduction of medications to the patient, and increase the potential for bleeding or infection at the catheter incision site. If extensive movement occurs, the PICC line could even come out of the patient, interrupting delivery of medication and requiring re-insertion, often with hospitalization.

In the past, catheters were simply taped into place on the patient's skin. However, taping is time consuming and labor intensive. Tape also collects bacteria and must be frequently removed and replaced. More importantly, taping is not necessarily effective in securing a catheter in place. Sutures have also been used to attach a catheter to a patient. With sutures, the catheter is stitched onto the skin. Sutures, however, can also be a source of infection, can cause pain and inflammation, and can make it more difficult to clean around the incision site. Sutures also require time and skill to place, and can cause scarring.

More recently, manufactured catheter anchors or securing devices have come into more widespread use. These devices are specifically designed to secure specific catheters in place. While various designs have been used, these devices generally have an adhesive-backed pad that bonds to the skin over a large area. The catheter is secured into or onto a catheter anchor designed for holding the catheter. These anchoring devices have various advantages over tape or sutures. However, engineering design challenges remain in providing reliable, secure and efficient anchoring devices. Further, because existing anchoring devices are generally designed for a specific type of catheter, multiple anchors may be needed to accommodate use of different types of catheters, e.g., in hospitals and clinical settings. This adds to the cost and complexity of sourcing, inventory, storage, and selection of the anchoring devices. Accordingly, improved anchoring devices are needed.

SUMMARY OF THE INVENTION

A substantially universal catheter securing device may have a base with one or more locating elements, such as walls or pegs. The locating elements on the base may be positioned and arranged for securing and positioning catheters and catheter fittings of various shapes and sizes. The base, which may be attached to an adhesive pad, is connected or connectable to a cover having capture elements. The capture elements may grip and compress a catheter fitting when the cover is in a closed position, thereby helping secure a catheter and catheter fitting of various sizes within the universal catheter securing device. In an alternative design, the locating elements can be omitted, with the catheter secured in the device largely via only compression and friction forces resulting from clamping the catheter between the base and a cover. Another design for holding catheters and the like in place may include locating or positioning elements on a base and contact surfaces on a cover.

BRIEF DESCRIPTION OF THE DRAWINGS

In the drawings, the same element number indicates the same element in each of the views.

FIGS. 22-29 are plan views of various catheter fittings positioned on the base and within the locating elements of the securing devices shown in FIGS. 1-2 and 10.

DETAILED DESCRIPTION OF THE DRAWINGS

A universal securing device for holding catheters of various designs may include a base and a cover. The cover may be connected to the base by a hinge which allows the cover to be lifted open or pushed down into a closed position, to secure a catheter fitting or similar device. The base and/or cover have locating elements configured and arranged to fit around catheters and catheter fittings of various shapes and sizes. The catheter fitting is placed into or onto the base from above. The locating elements prevent substantial movement of a catheter and/or catheter fitting in multiple dimensions.

Latching elements, which may be located on squeezing arms hold the cover onto the base. Capture elements may be located on the under side of the cover to compress a catheter fitting, securely holding it in place against the base, in the closed position. The catheter may be held securely in place on a patient once the securing device is attached to the patient. The catheter can be removed from the base by disengaging the latching elements, for example, here by squeezing the squeezing arms toward each other. Thus, a catheter and catheter fitting of various shapes and sizes can be securely held by a single securing device and can be quickly and easily attached to or removed from the patient. The devices described herein may be used with, e.g., PICC lines, IV catheters, Foley catheters, heart catheters, J-loops, and various others. In addition to a catheter, the present securing device may be used to secure other tubes, cables, wires, and various other medical devices as well.

Figure 1:
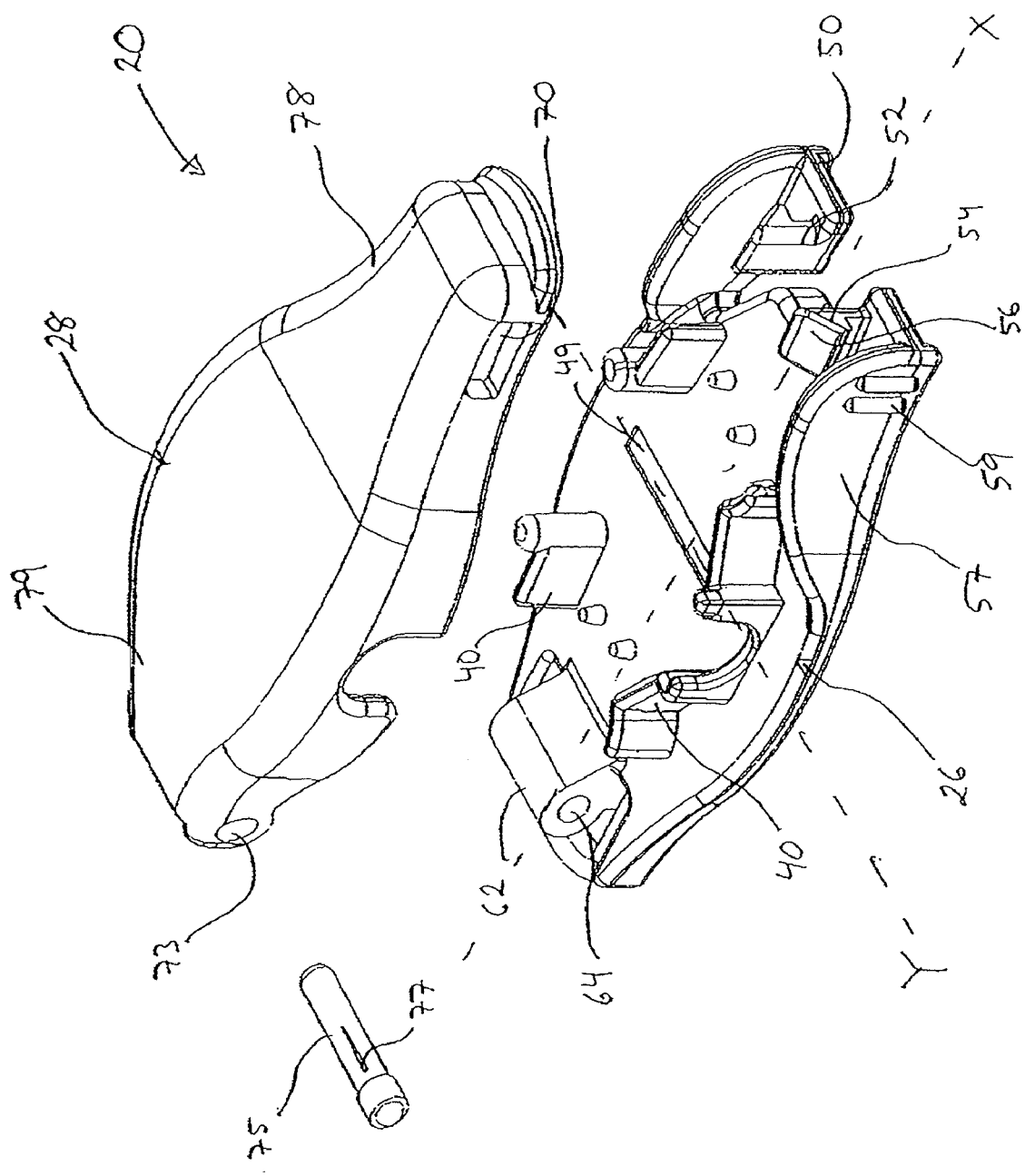
FIG. 1 is an exploded perspective view of a securing device.
Figure 2:
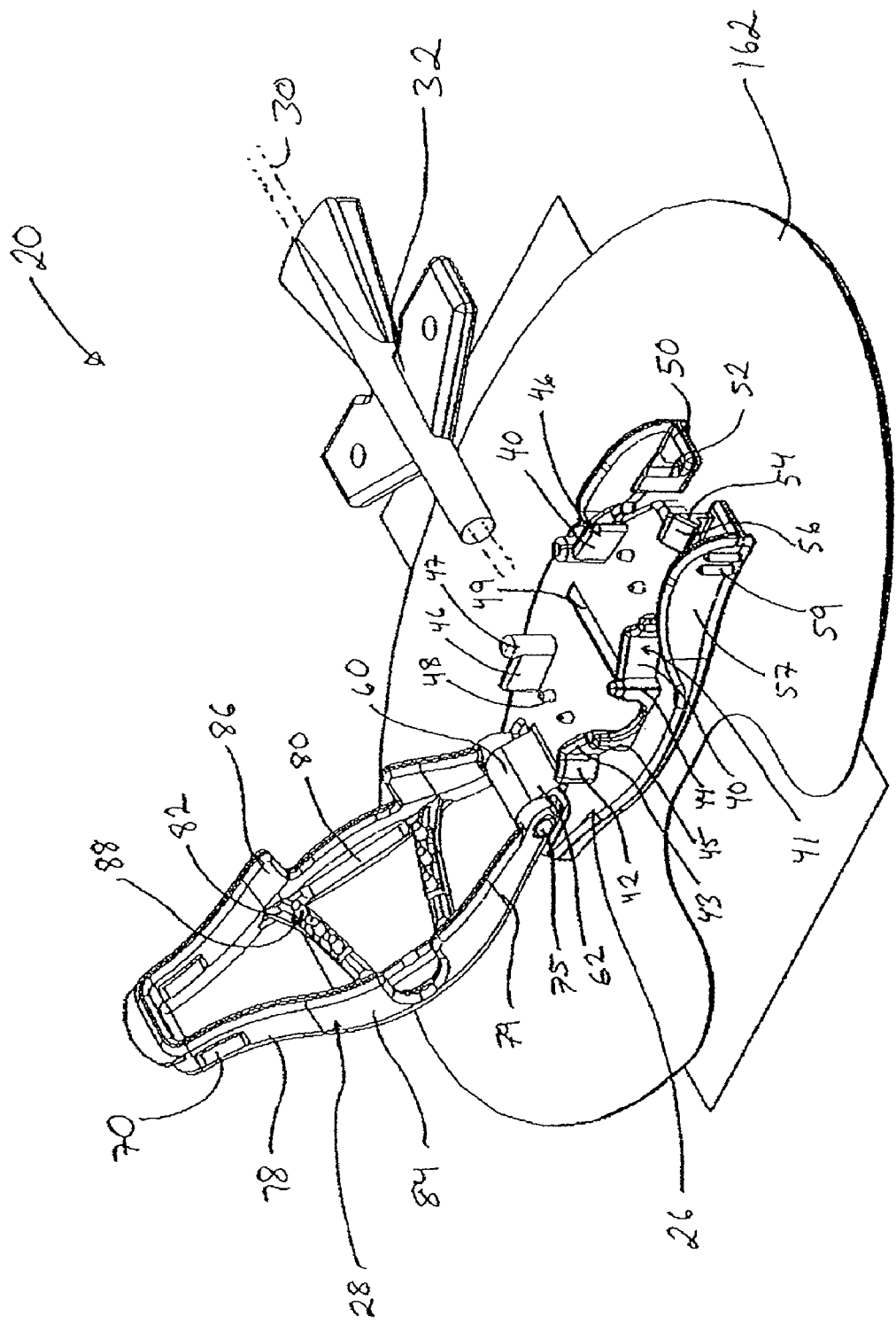
FIG. 2 is a top and front perspective view of the device shown in FIG. 1, with the cover lifted in an open position and base attached to an adhesive pad.

Turning now to the drawings, as shown in FIGS. 1-9, a securing device 20 has a base 26. As shown in FIG. 2, the base 26 may be contoured and may have one or more locating elements 40 which are shaped and dimensioned to be positioned around and hold catheters and catheter fittings of various shapes and sizes, such as catheter fitting 32 and catheter 30. In FIGS. 2-5 and 8-9, the locating elements 40 include rectangular shaped walls, however, locating elements may be round, square, hexagonal, etc. and they may take on various forms in addition to walls such as pegs, columns, etc. The base may vary in size and typically is about 2-3 inches long and about 1-2 inches wide.

Figure 3:
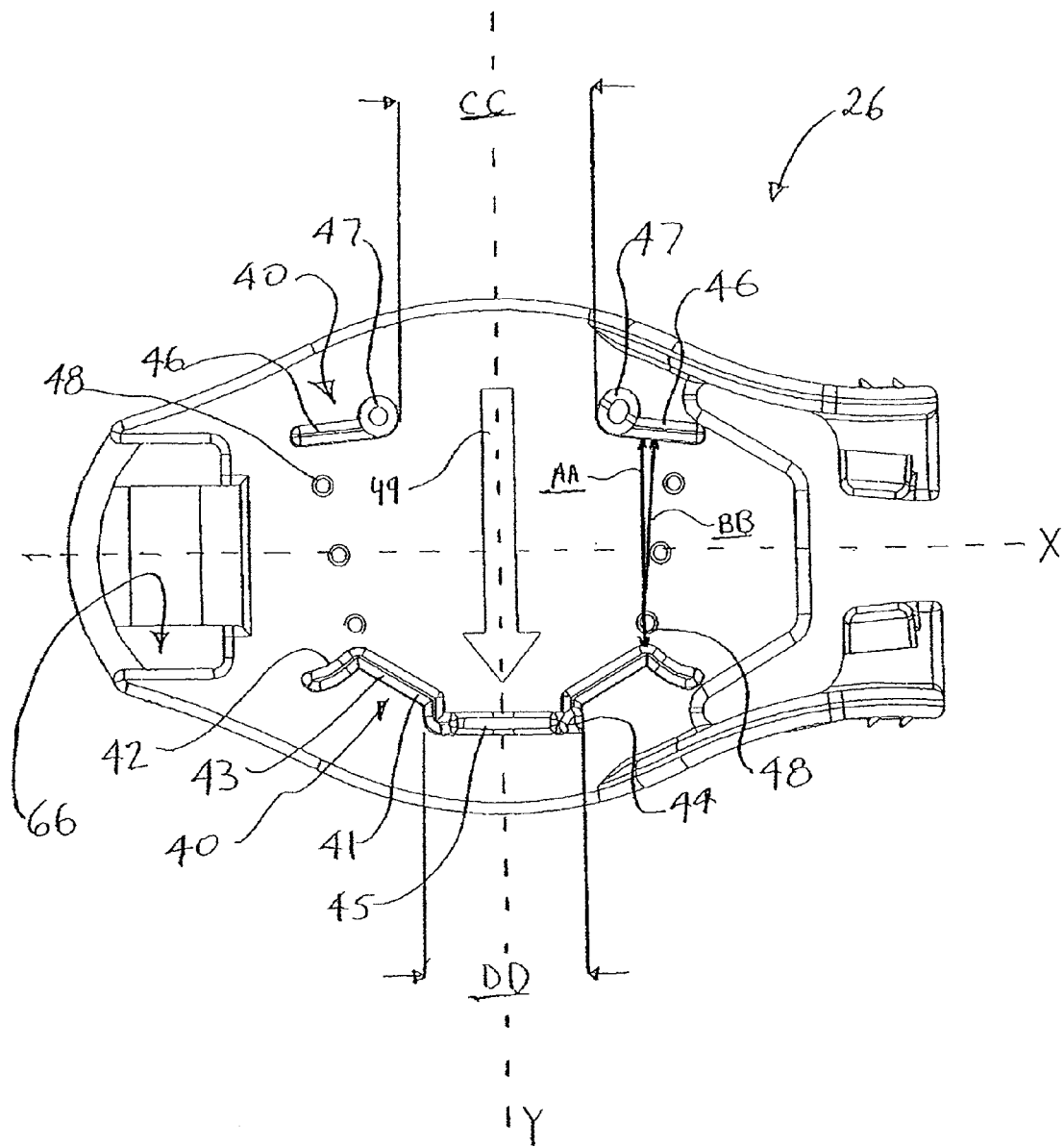
FIG. 3 is a plan view of the top surface of the base and locating elements of a securing device shown in FIGS. 1-2.
Figure 4:
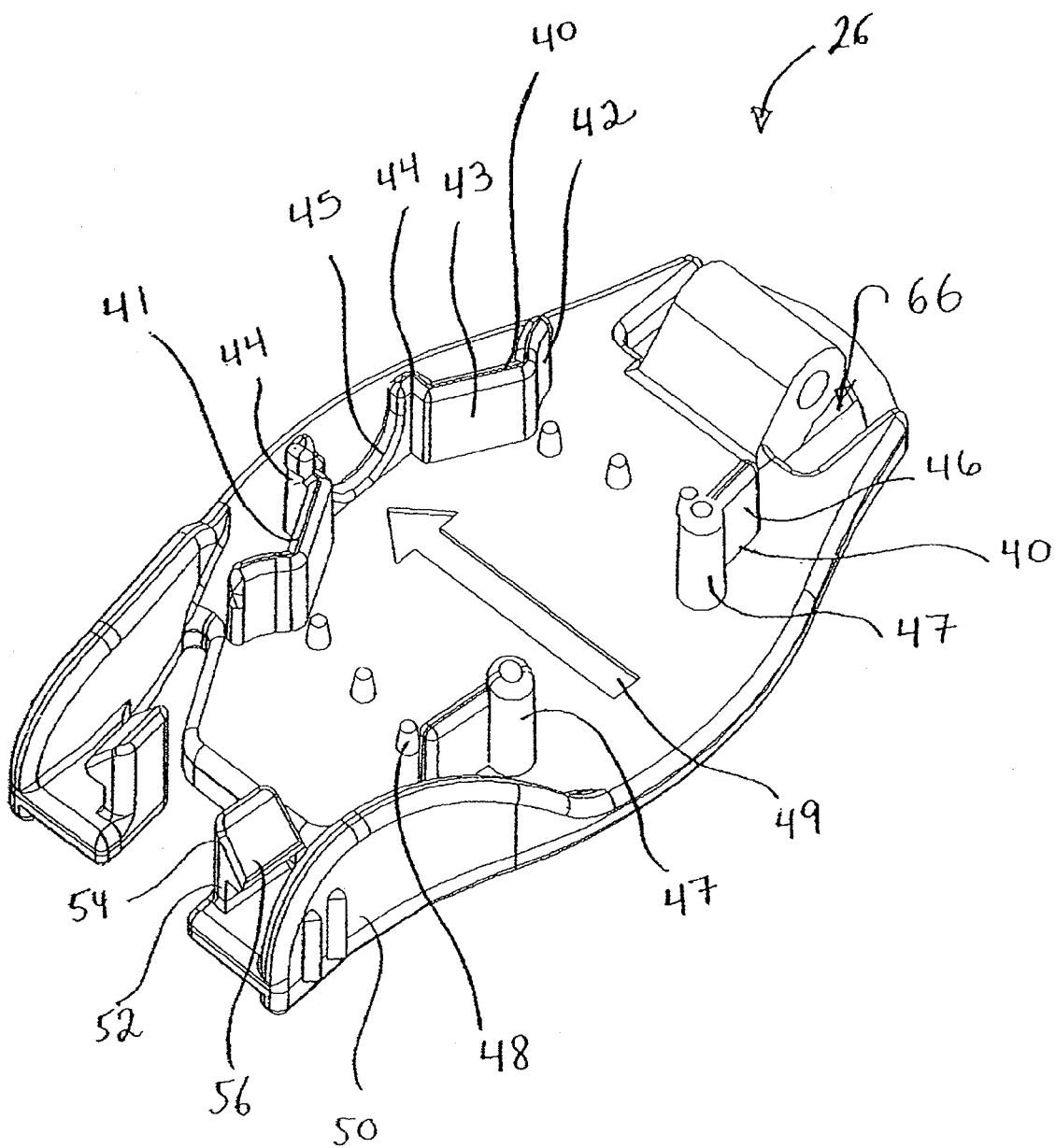
FIG. 4 is top and front perspective view of the base shown in FIGS. 1-3.
Figure 5:
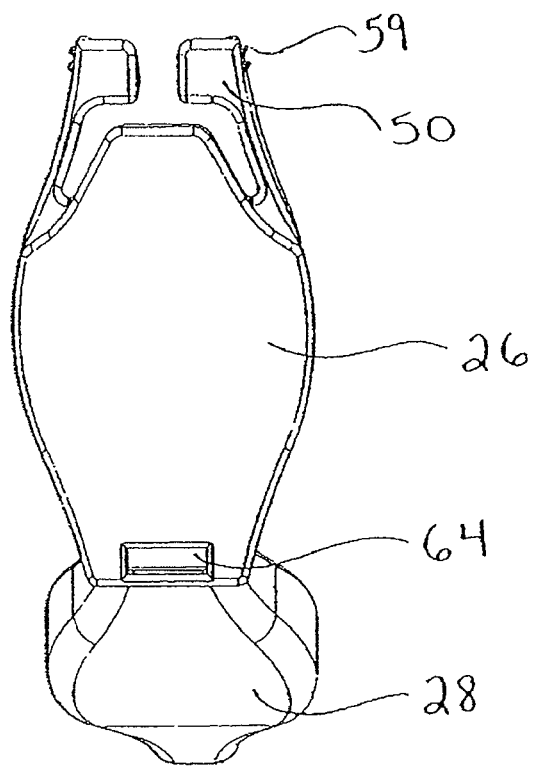
FIG. 5 is a back perspective view showing the bottom surface of the base shown in FIG. 4.

Referring to FIGS. 3-4, the locating elements 40 extend up from the base 26. In this particular embodiment, the locating elements include at least one front wall 41 and a pair of back walls 46. The front and back walls are spaced apart in a front to back direction as indicated by arrow 49, which runs along a longitudinal axis identified by the imaginary line marked Y shown in FIG. 3. A front wall 41 shown in FIGS. 3-4 is made up of at least one curved end wall 42, at least one angled front wall 43, at least one elbow 44. A semicircular trough 45 may be positioned slightly forward of the angled front wall 43 as indicated by arrow 49 and may be connected to the elbow 44. A raised post may extend up from at least one elbow 44. The back walls 46 are preferably angled and are each connected to a post 47. The first and second posts 47 connected to either back wall 46, can be the same size or they may differ in size. In general, the locating elements 40 may be substantially symmetrical side-to-side about the longitudinal axis or centerline Y. The locating elements 40 are arranged and positioned to allow PICCs and other catheters of various shapes and sizes to be placed onto the base 26 and held within the securing device 20. The locating elements 40 are arranged in a manner to help position catheters and catheter fittings of various shapes and sizes and prevent substantial movement of a catheter and catheter fitting in various dimensions relative to the base, e.g., side-to-side and back-to-front, axial movement, as well as rotational movement.

Referring to FIGS. 3-4, in one embodiment the locating elements 40 are arranged such that a front wall 41 is separated from the back wall 46 by a dimension AA which extends straight back, parallel to the longitudinal Y axis, from the rear most tip of curved end wall 42 of front wall 41 to the back wall 46. The front wall 41 may also be separated from the back wall 46 by a dimension BB which extends from the rear most tip of curved end wall 42 of front wall 41, straight back and perpendicular to the back wall 46. Also, the inner edge of the first or left post 47 may be separated from the inner edge of the second or right post 47 by a dimension CC running generally parallel to a lateral axis X. Also, the first or left elbow 44 may be separated from the second or right elbow 44 by a dimension DD running parallel to dimension CC.

In one embodiment, dimension M may be less than dimension BB. Also, dimension CC may be greater than dimension DD. In another embodiment dimension AA may measure about 0.34 to 0.38 inches, preferably 0.35 to 0.37 inches, or more preferably 0.36 inches in length. Dimension BB may measure about 0.37 to 0.41 inches, preferably 0.38 to 0.40 inches, or more preferably 0.39 inches in length. Also, dimension CC may measure about 0.35 to 0.39 inches, preferably 0.36 to 0.38 inches, or more preferably 0.37 inches in length and dimension DD may be about 0.28 to 0.32 inches, preferably 0.29 to 0.31 inches, or more preferably 0.30 inches in length. In another embodiment, dimension CC may be about 130 to 170% of dimension DD or more preferably about 140 to 160% of dimension DD.

Referring to FIGS. 3-4, the base may also include one or more spikes 48 extending up from the base. In one embodiment, a line of posts or spikes 48, are located on a line between front wall 41 and back wall 46, on both sides of axis Y. The line of posts or spikes 48 may be generally parallel to each other and to the longitudinal axis Y or at an angle of, e.g., 1-45° to the longitudinal axis Y. The spikes 48 may extend up from the surface of the base or from capture elements running generally parallel to each other and to the longitudinal axis Y or at an angle of, e.g., 1-45° to the longitudinal axis Y, on both sides of axis Y between a front wall 41 and a back wall 46.

Referring to FIG. 1, the base 26 may have two squeezing arms 50 or optionally the base 26 may have one arm 50 that is resilient and flexible and a second arm 50 which is generally fixed and rigid. The base 26 may also have a hinge block 62 located on the base 26 at an opposite end from the squeezing arms 50. The squeezing arms 50 are flexible and have latching elements 52 and sidewalls 57. An angled surface 56 may be provided at the end 54 of each of the latching elements 52 facing the inner surface of a squeezing arm wall 57, with grip ribs 59 on the outside of each squeezing arm wall 57. As shown in FIG. 3-4, a through hole 66 may be provided, if desired, in the base 26, behind the hinge block 62. An arrow symbol 49 may be printed, molded or otherwise provided on the base 26 and/or the cover 28, running along a longitudinal Y axis, as shown in FIG. 3. The arrow indicates in which direction the catheter should be installed into the universal securing device 20.

As shown in FIG. 1, the cover 28 has latch holes 70, and hinge pinholes 73 located at opposite ends of the cover 28. Ridges 71, each having an angled surface 72, may optionally be provided below the latch holes 70, as shown, e.g., in the embodiment of FIG. 10. As shown in FIG. 2, the cover 28 is connected to the base 26 by a hinge 60. FIG. 1 shows that the hinge may be provided by pressing a hinge pin 75 through hinge pinholes 73 and through an aligned hinge pin slot 64 which runs through the hinge block 62. The hinge pin 75 may have a round diameter and may include one or more, preferably four, raised crush ribs 77 which serve to hold the hinge pin 75 in place by friction after being press fit through the hinge pinholes 73 and hinge pin slot 64. The hinge may also take various other forms, for example, a hinge may be formed by tongue and groove elements. A hinge may also be formed by a snap fitting mechanism between a latch or snap hinge and snap hinge base. Various types of hinges or pivot joints may be used. Most designs will have a hinge at one side of the device and a latching element at the other side, with the cover pivoting open and closed. However, an alternative design may have a separate snap on cover having a latch or lock element at either end of the cover.

Figure 6:
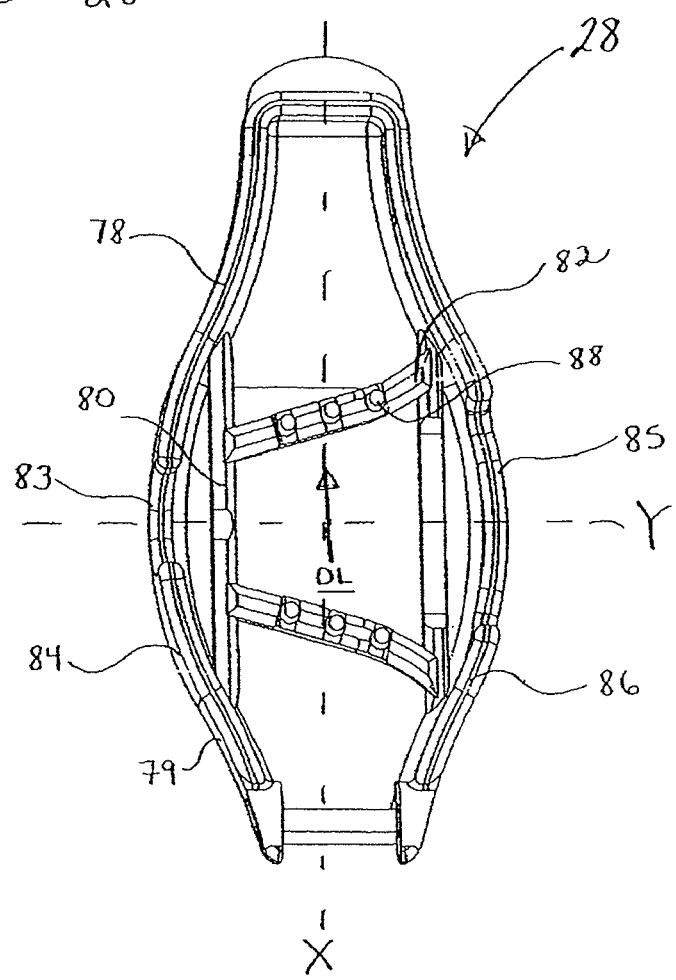
FIG. 6 is a plan view of the under side of the cover shown in FIGS. 1-2 and 5.
Figure 7:
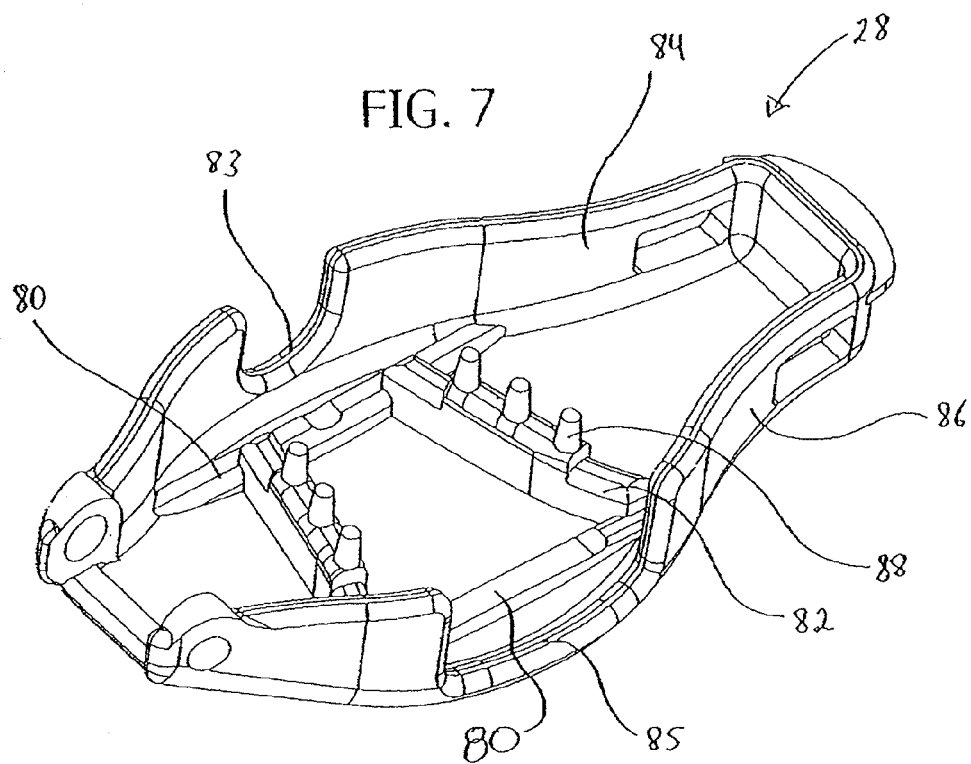
FIG. 7 is a top and back perspective view of the under side of the cover shown in FIGS. 1-2 and 5.
Figure 8:
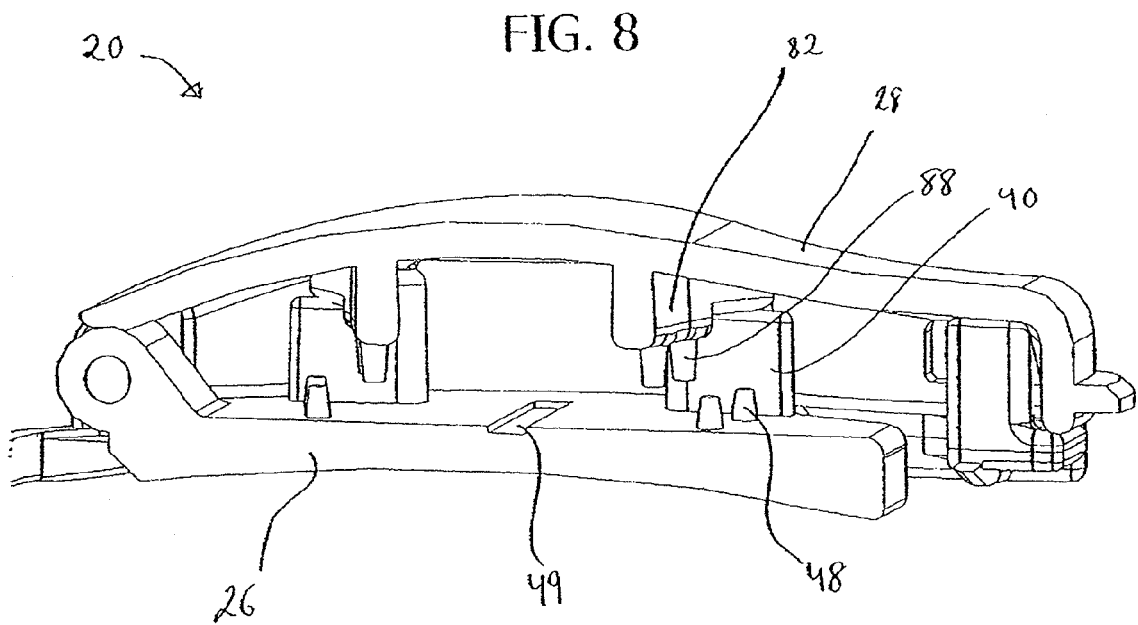
FIG. 8 is a cross section of a side perspective view of the securing device shown in FIGS. 1-2 and 5 in a closed position.

As best shown in FIGS. 6-7, the cover 28 includes a first opening 83 in a front wall 84 and a second opening 85 in a back wall 86. The cover 28 may have one or more bars 80 which run in a direction DL on the underside of the cover 28, generally parallel to the lateral X axis. The center area of the bars 80 may be recessed compared to the ends of the bars 80 in order to accommodate the height of various catheter fittings. The bars 80 may be connected by one or more capture elements 82 on the underside of the cover 28. The capture elements 82 may be generally parallel to each other and to the longitudinal Y axis, or at an angle of, e.g., 1-45° to the longitudinal axis. The ends of the capture element 82 may rest at least partially on the surface of the bars 80. One or more posts or spikes 88 may extend from the capture elements 82. In the design shown in FIG. 7, three spikes 88 are spaced evenly apart and extend up from a center elevated segment 86 on the surface of the capture element 82. Optionally, the capture elements 82 may run along the underside of a cover where the cover has no bars.

Turning momentarily to FIG. 2, the capture element 82 is adapted to contact and compress catheter fittings of various shapes and sizes such as catheter fitting 32, e.g., by compressing the wings and/or body of a catheter fitting 32 once the catheter fitting 32 is placed onto the base 26 within the locating elements 40 and the cover 28 is attached to the base 26 in a closed position. Capture elements 82 may be solid or spring molded as leaf springs or foam springs. Capture elements 82 may also be an elastomer. The surface of a capture element 82 may optionally be provided with cones or serrated teeth to assist with compression and gripping of a catheter fitting 32. A single capture element 82 or multiple capture elements 82 may be used. In the specific design shown if FIG. 2, two capture elements are provided.

Referring again to FIGS. 2 and 4, in use, after the catheter has been inserted into the patient, the skin at the securement site is preferably cleaned. The catheter fitting 32 is then placed into or onto the base 26, within the locating elements 40. The cover 28, which is attached to the base 26 via the hinge 60, can be closed down, by pivoting about the ends of the hinge pin 75 positioned inside the hinge block 62, over and onto the catheter fitting 32. The curved end wall 42, elbow 44 and semicircular trough 45, all serve to center and align the cover 28 as the cover 28 is moved down and over the front wall, onto the base 26, and into the closed position. The outside surface of the curved end wall 42, elbow 44 and semicircular trough 45 may abut against the inner surface of the front wall 84 of the cover 28 as the cover 28 moves down and into the closed position. Also, a raised post which may be located atop one or more elbows 44 may also help align the cover 28 as it closes onto the base 26, and it too may optionally abut against the inner surface of the front wall 84 of the cover 28 as the cover 28 moves down and into the closed position. Also, one or both of the posts 47 connected to a back wall 46 may serve to center and align the cover 28 as the cover 28 is moved down and over a back wall 46 and the first and second posts 47. The first and second posts 47 and back walls 46 may abut against the inner surface of the cover 28 as the cover 28 moves down and into the closed position. These alignment features help to properly locate the cover on the base as the cover is closed.

Figure 9:
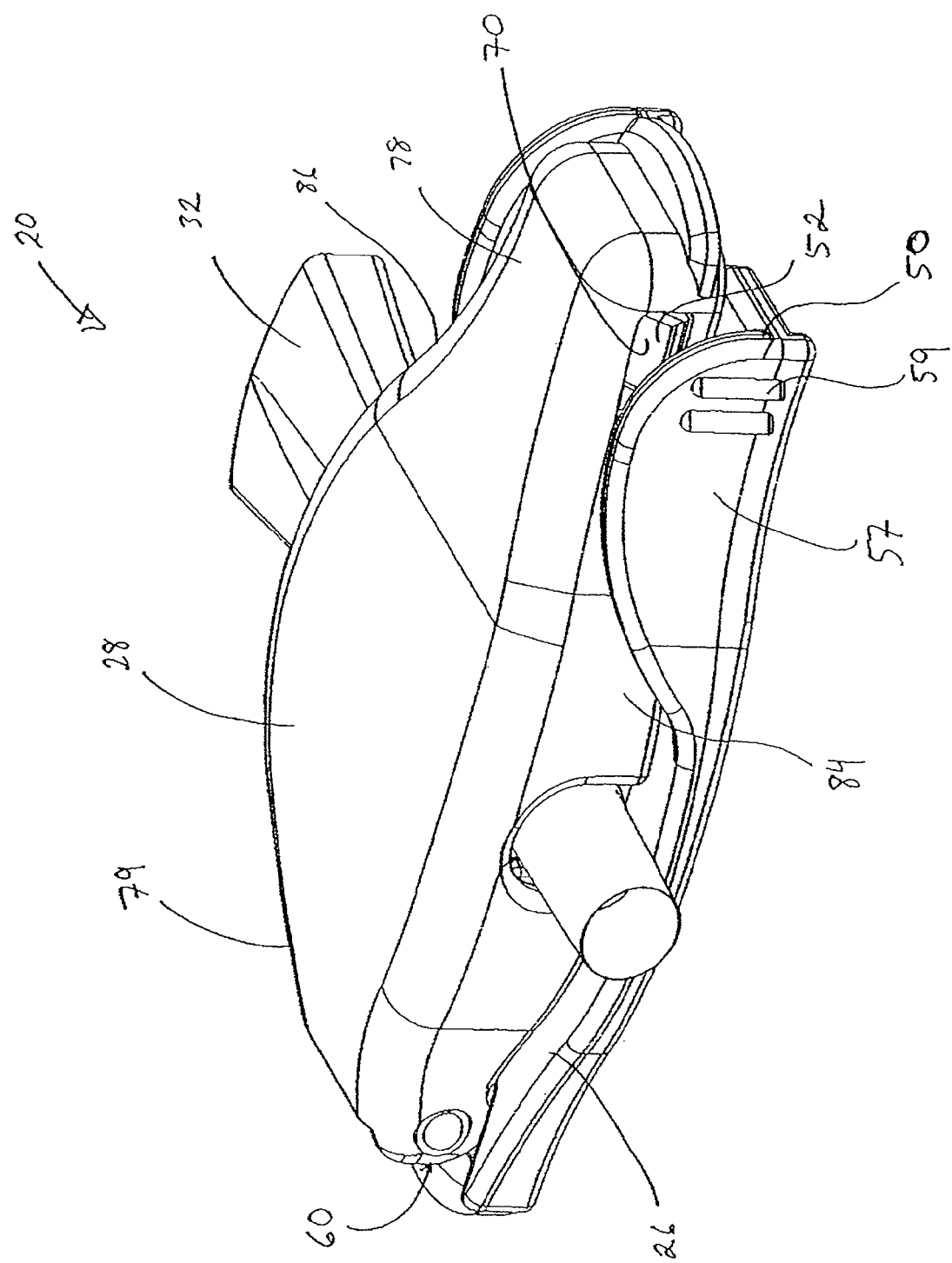
FIG. 9 is a top and front perspective view of the device shown in FIGS. 1-2 and 5 in a closed position.

In a closed position (as shown in FIG. 9), the top end 78 of the cover 28 attaches to the base 26 within the squeezing arm walls 57. The latch holes 70 in the front wall 84 and back wall 86 of the cover 28 engage the latching elements 52 on the squeezing arms 50. This facilitates the secure attachment of the cover 28 to the base 26, placing the securing device 20 in a closed position. The cover 28 rests on the flat and contoured outer areas of the base 26, around the front wall 41 and back walls 46 (not shown because enclosed by cover), and on the flat area of the squeezing arms 50.

In a closed position, the spikes 88 on one or more capture elements 82 may compress down on the wings and/or body of the catheter fitting 32. The wings of the catheter fitting 32, which are generally somewhat flexible or compliant, are thereby pinched or held between the spikes 88 of capture element 82 and the spikes 48 extending up from the surface of the base 26. The spikes 88 and the spikes 48 are located to grip and compress the wings and/or body of the catheter fitting. As shown if FIG. 8, the spikes 88 and spikes 48 are preferably about 0.04 inches in height and some vertical space may exist between the tips of the spikes 88 and the spikes 48 when the cover 28 is in the closed position. The spikes 88 may also be slightly offset by 0.02-0.12 inches to the inside of the spikes 48, i.e., toward the arrow 49. The spikes 88 may also be similarly offset to the front of the spikes 48, as indicated by arrow 49. This applies a pinching or bending effect on the wings of the catheter, in addition to compression. By having the top and bottom spikes offset from each other, the device 20 can better secure catheters having wings of varying thickness.

The capture elements 82 thereby secure a catheter fitting 32 within securing device 20 by preventing substantial movement of catheter fitting 32 in an axial, side-to-side, back-to-front, up and down and rotational direction. The capture element 82 may be resilient and flexible, capable of holding and griping catheter fittings of various thicknesses. The capture element 82 may also be solid. The cover 28 may be used in conjunction with a base 26, having locating elements 40 and spikes 48, for securing a catheter fitting.

In another embodiment, the cover 28 may be used in conjunction with a base 26 for compressing and holding a catheter body on a patient. The base may or may not have locating elements. In use, this embodiment would function by placing a catheter on a base 26 and compressing or pinching the catheter body between an underside surface of a cover 28, e.g., against capture elements 82 or any part of the underside of the cover, and a top surface of the base with sufficient force to hold or restrain the catheter in place without substantial movement in various dimensions relative to the base and cover, e.g., axial, side-to-side, back-to-front, up and down and rotational. This arrangement, for compressing a catheter body of various shapes and sizes between a cover and base could be performed with any of the additional embodiments described below as well.

Figure 10:
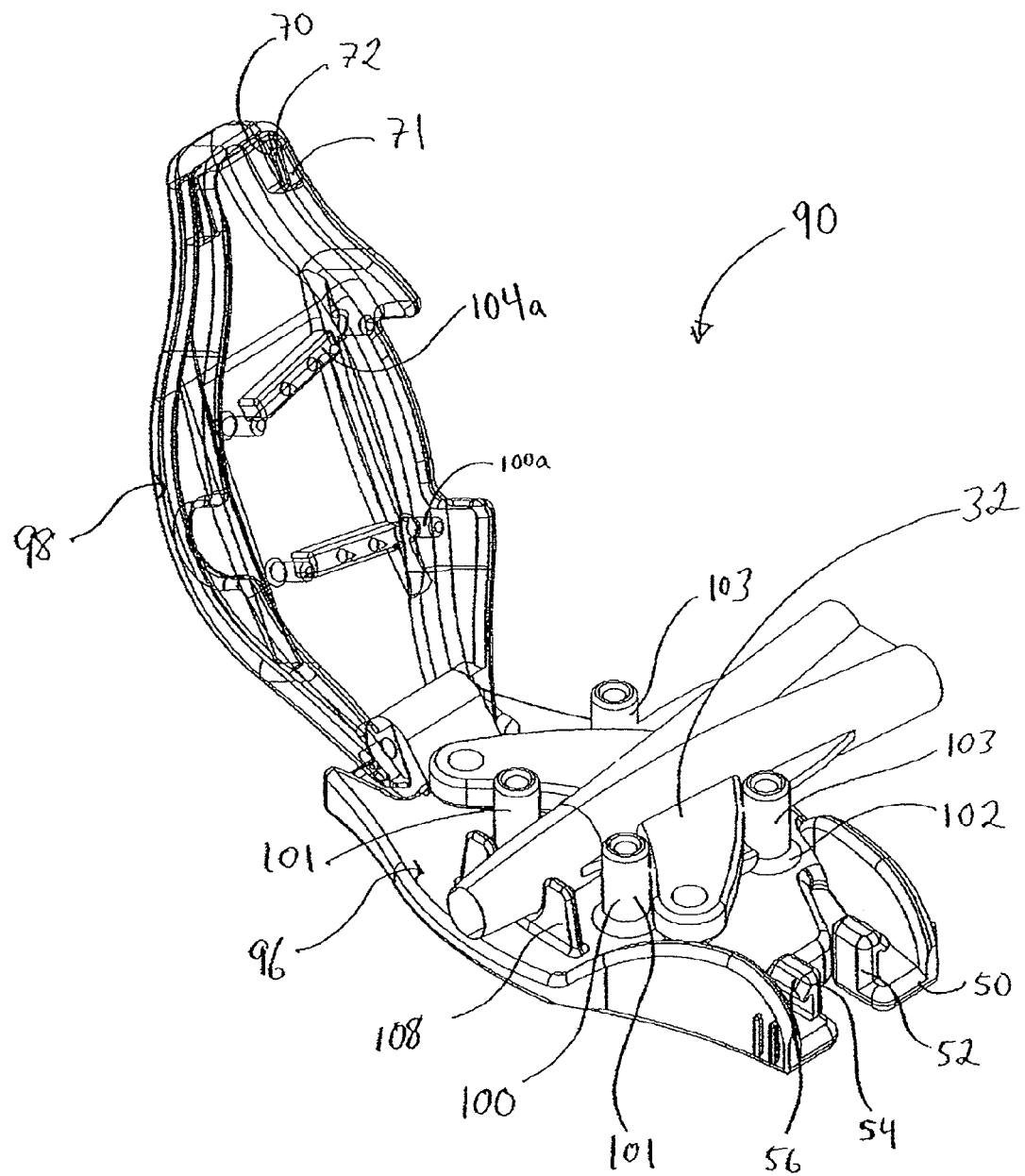
FIG. 10 is a top and front perspective view of another embodiment of a securing device with the cover lifted in an open position.

Referring again to FIGS. 2 and 4, as the top end 78 of the cover 28 is moved down onto the base 26 from an open position to a closed position, the angled surfaces 56 on the ends 54 of the latching elements 52 engage the inner surface of the front wall 84 and back wall 86, below the latch holes 70 on the cover 28. Alternatively, the angled surfaces 56 on the ends 54 of the latching elements 52 may engage the angled surfaces 72 of ridges 71, positioned below the latch holes 70 on the cover 28, e.g., as shown in the embodiment of FIG. 10. The latching elements 52 are somewhat resilient and can flex slightly under load in the longitudinal direction (along axis Y as shown in FIG. 1). As a result, as the cover 28 is moved down into engagement with the base 26, the latching elements 52 flex slightly inwardly toward each other. The angled surfaces 56 of the latching elements 52 and the inner surface of the front and back walls 84, 86 below the latch holes 70 on the cover 28 or the angled surfaces 72 of the ridges 71 slide against each other and pass by each other. The latching elements 52 then flex back to near their original longitudinal positions, forcing the ends 54 of the latching elements through the latch holes 70 in the cover 28 and locking the cover 28 onto the base 26. The catheter securing device 20 is then attached to the patient at the prepared securement site, usually via an adhesive pad. The securing device 20 then prevents virtually any movement of the catheter fitting 32 and adjoining catheter 30 within the securing device.

The catheter 30 may be removed by squeezing the squeezing arms 50 together, towards each other. One or both of the squeezing arms 50 may be resilient and flexible such that they may flex in the longitudinal direction. The squeezing arms 50 may be squeezed together by applying a force in the longitudinal direction, generally on the area of the grip ribs 59 located on the outer surface of the squeezing arm walls 57. Squeezing also causes the latching elements 52 on the squeezing arms 50 to move longitudinally toward each other, resulting in the ends 54 of the latching elements 52 moving back through and out of the latch holes 70. The latching elements 52 move toward each other such that the cover 28 can be lifted away from the latching elements 52. The angled surface 56 and angled surface 72 and/or inner surface of the cover 28 pass by each other as the cover 28 is pivoted up and off of the base 26.

The securing device described above may be attached to a patient in a variety of ways. As shown in FIG. 1, a base 26 may be attached to a pad 162 which is flexible to conform to the patient's arm or other site. The pad could be a hydro colloidal pad. The specific pad shape and size is not essential and various alternatives may be used. In FIG. 1, the pad 162 is generally oval or round and it can also be a small footprint of a base 26. The back side of the pad 162 preferably has one or more peelable strips over an adhesive layer or surface. The peel strips may be removed from the back of the pad 162, and the pad placed onto a prepared securement site. A cut out 164 may be provided at the front of the pad 162 to allow the base 26 to be closer to the incision or catheter entry point. Alternatively, the securing device may be affixed directly to a patient by applying adhesive tape around the device and against the patient's arm or other site.

Figure 11:
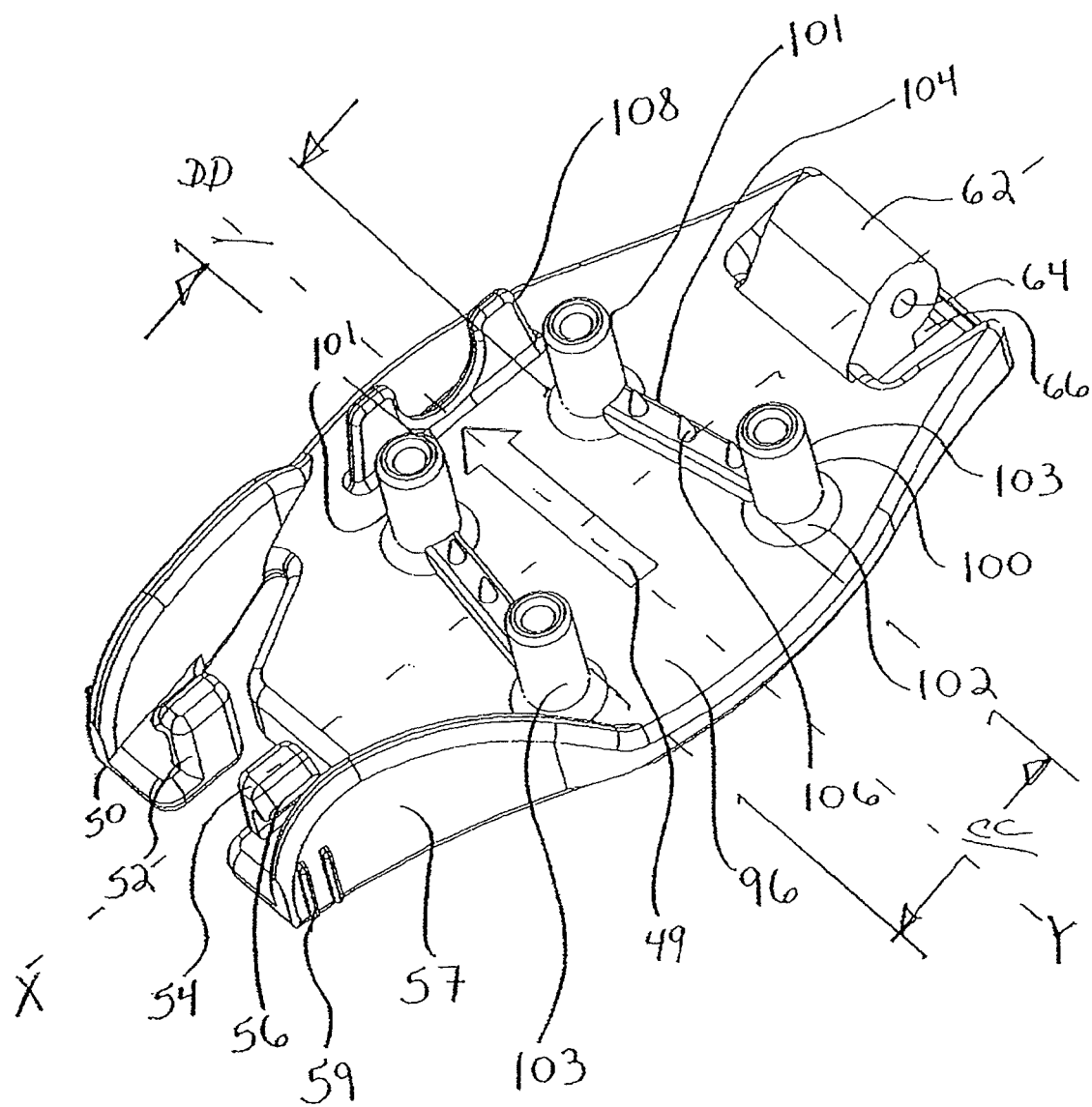
FIG. 11 is a top perspective view of the base of the securing device shown in FIG. 10.

FIG. 10 shows another embodiment 90 of a universal securing device. Securing device 90 has a base 96 and a cover 98. In this embodiment, as shown in FIG. 11, the locating elements extending up from the base 96 are locating pegs 100 and each peg is surrounded by a ridge 102 at the base of the peg. A front pair 101 and back pair 103 of locating pegs extend from the base 96 and are arranged in a configuration to position and hold a catheter and catheter fitting of various shapes and sizes and prevent substantial movement of such catheters and catheter fittings in various dimensions, similar to locating elements 40 described above.

As with the locating elements 40 shown above in FIG. 3, a first back locating peg 103 may be separated from a second back locating peg 103 by a dimension CC, while a first front locating peg 101 may be separated from a second front locating peg 101 by a dimension DD, as shown in FIG. 11. In one embodiment dimension CC may be greater than dimension DD. In another embodiment dimension CC may measure about 0.35 to 0.39 inches, preferably 0.36 to 0.38 inches, or more preferably 0.37 inches in length and dimension DD may be about 0.28 to 0.32 inches, preferably 0.29 to 0.31 inches, or more preferably 0.30 inches in length. In another embodiment, dimension CC may be about 130-170% of dimension DD or more preferably about 140-160% of dimension DD.

In addition, in FIG. 11, the locating pegs 100 positioned closest to the hinge block 62 and located above the arrow 49, may be connected generally horizontally by a capture element 104. The locating pegs 100 located below the arrow 49 and closest to the latching arms 50 may also be connected generally horizontally by a capture element 104. Spikes 106 may extend up from the surface of the capture elements 104. A semicircular trough 108, running generally parallel to the lateral axis X of the base 96 and positioned in front of the locating pegs 100 (as indicated by the arrow 49) may also extend up from the base 86. The spikes may optionally extend up from the surface of the base 86 in an embodiment without capture element 104.

Figure 12:
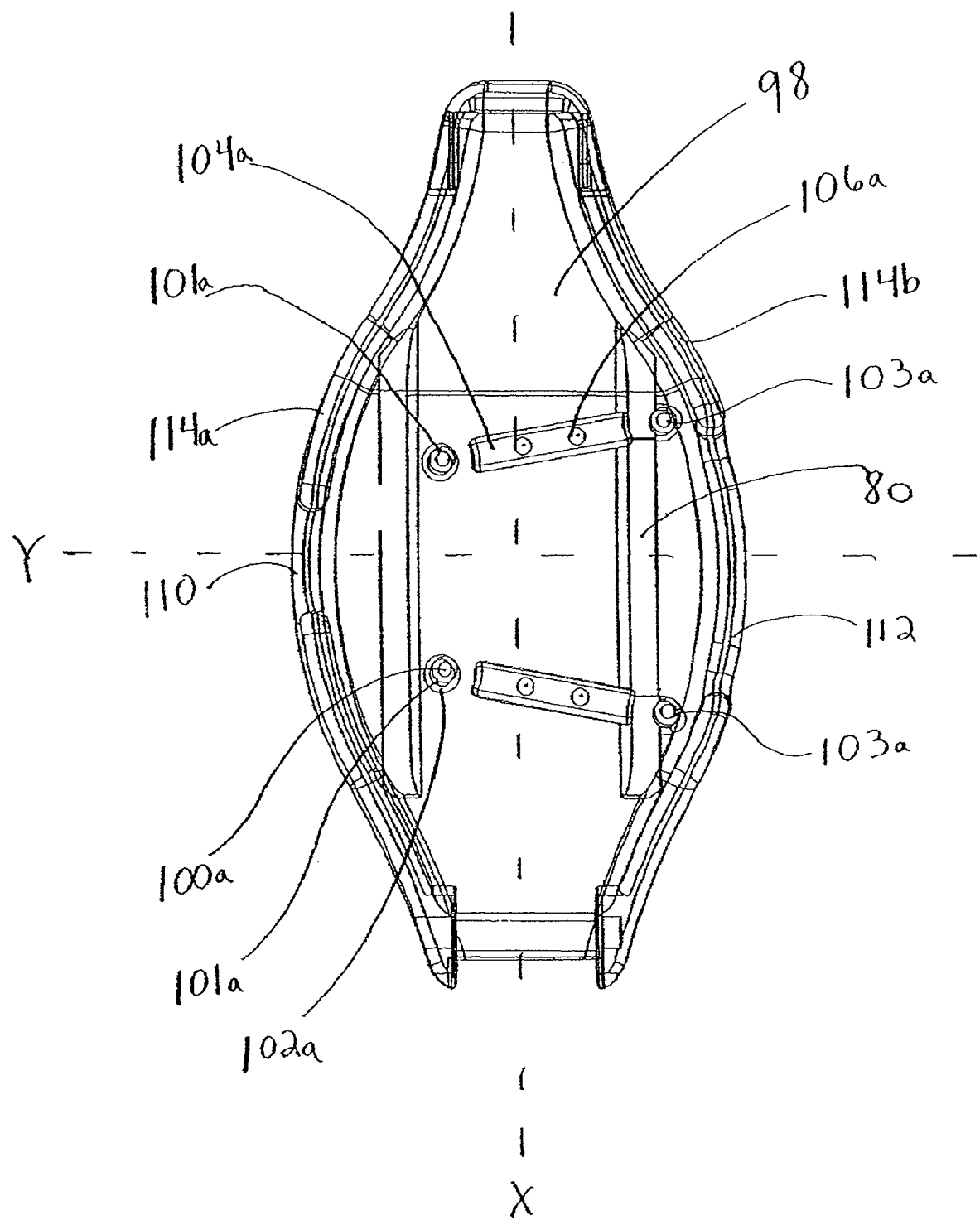
FIG. 12 is a plan view of the under side of the cover of the securing device shown in FIG. 10.
Figure 13:
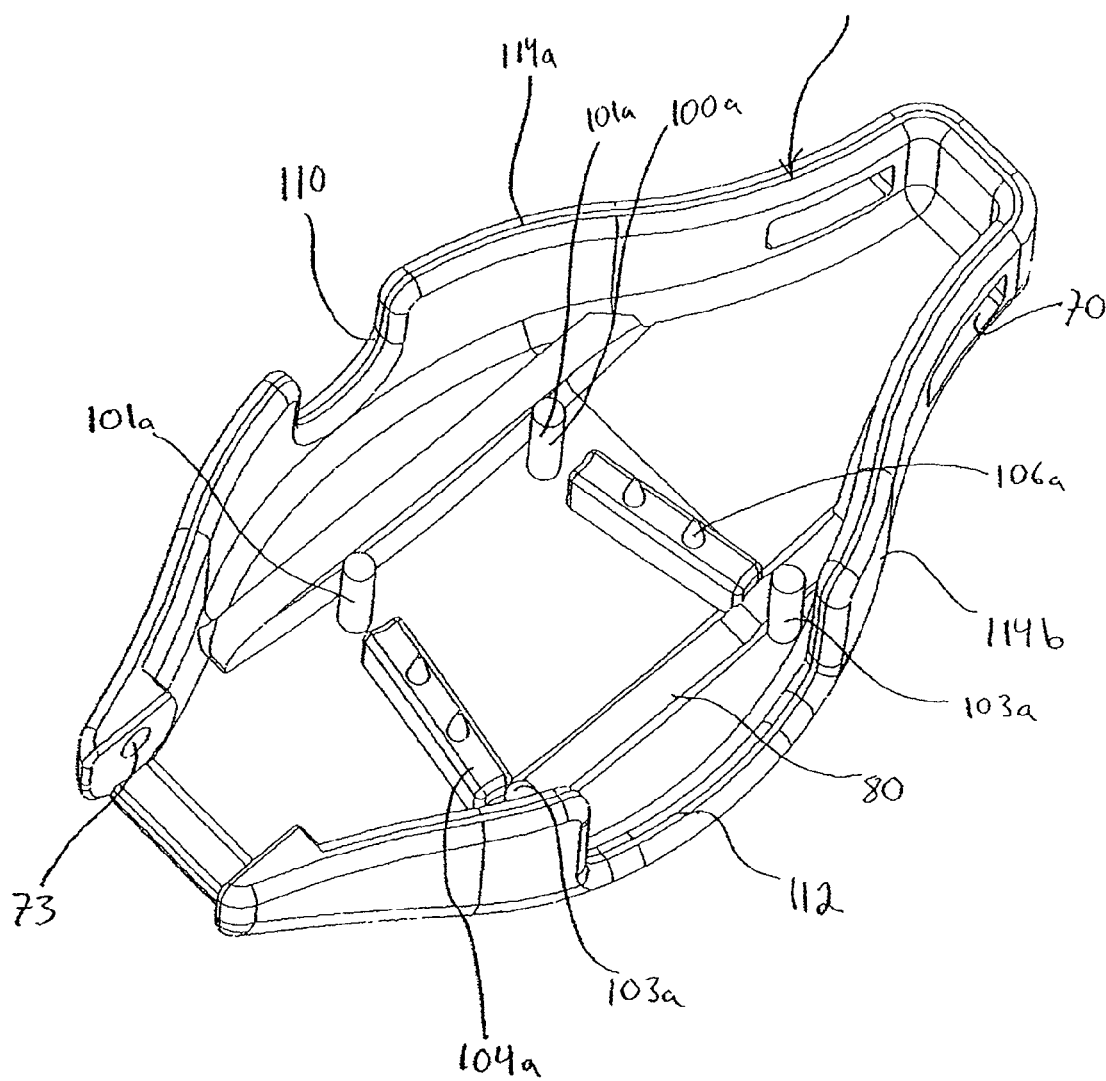
FIG. 13 is a top and back perspective view of the under side of the cover of the securing device shown in FIG. 10.

As shown in FIGS. 12-13, the cover 98 includes a first opening 110 in a front wall 114a and a second opening 112 in a back wall 114b. As best shown in FIG. 12 and with reference to the base 96 in FIG. 11, provided on the under side of the cover 98 are locating pegs 100a which are capable of fitting inside locating pegs 100 on base 96. The locating pegs on cover 98 include a front pair 101a and back pair 103a of locating pegs, each with ridges 102a as well at least one capture element 104a running between the locating pegs on the underside of the cover 98 arranged in a configuration that generally mirrors the configuration of locating pegs 100 and capture element 104 on the base 96. Spikes 106a may extend up from the capture elements 104a. The front pair 101a and/or back pair 103a of locating pegs may be positioned in between or outside bars 80, which are located on the underside of the cover 98 and run generally parallel to the lateral X axis (shown in FIG. 12). The capture elements 104 and 104a may be spring molded. Also, if desired, at least one locating peg 100a may be positioned at least partially on the surface of a bar 80. At least one capture element 104a may also be at least partially positioned on the surface of a bar 80. Father, with reference to FIG. 10, ridges 71, each having an angled surface 72, may optionally be provided below latch holes 70.

In one embodiment, the locating pegs 100a on the cover are connected by a capture element 104a which is positioned at an angle of about 1-45° to a longitudinal Y axis across the underside of the cover 98 and locating pegs 100 on the base 96 are connected by a capture element 104 which is positioned at an angle of about 1-45° to a longitudinal Y axis across the base.

Figure 14:
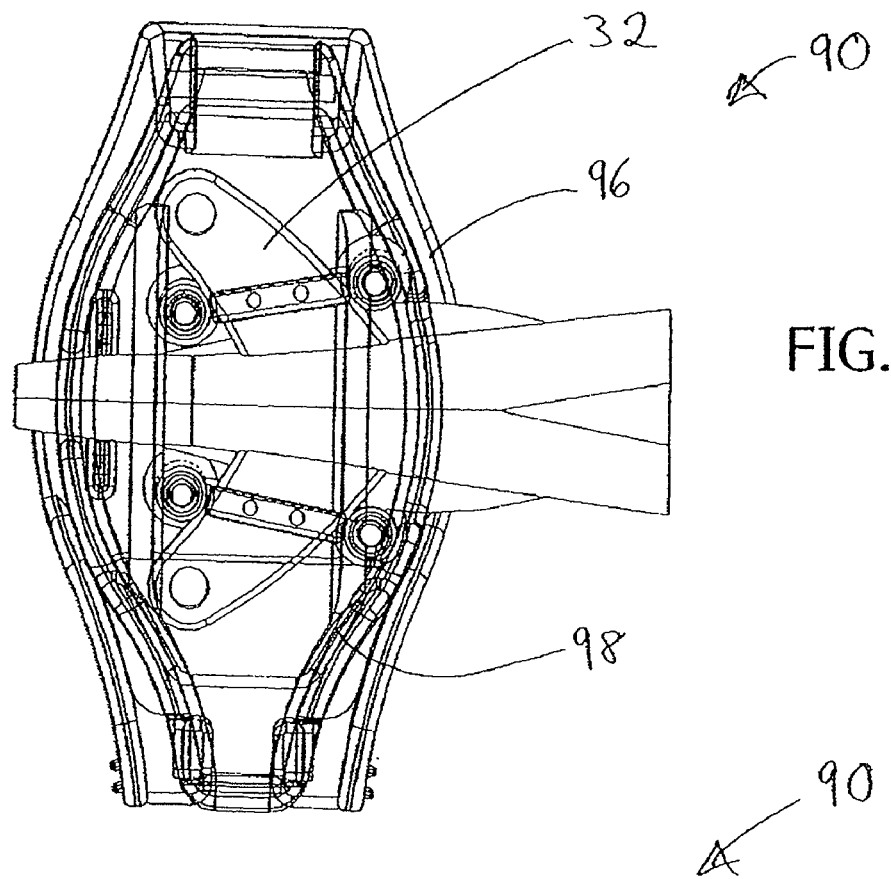
FIG. 14 is a plan view of the securing device shown in FIG. 10 in the closed position, holding a catheter fitting representative of various catheter fitting shapes and sizes.
Figure 15:
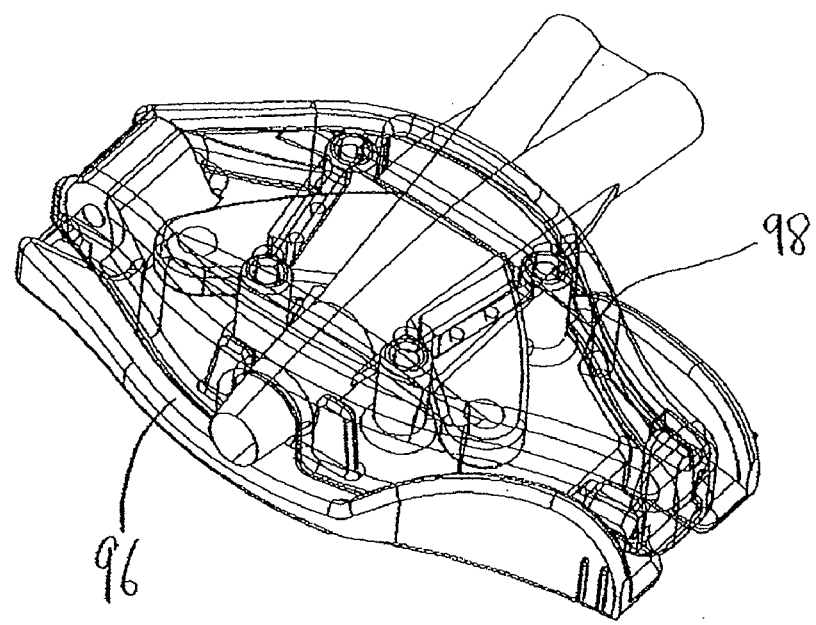
FIG. 15 is a top and front perspective view of the securing device shown in FIG. 10 in the closed position, holding an exemplary catheter fitting.
Figure 16:
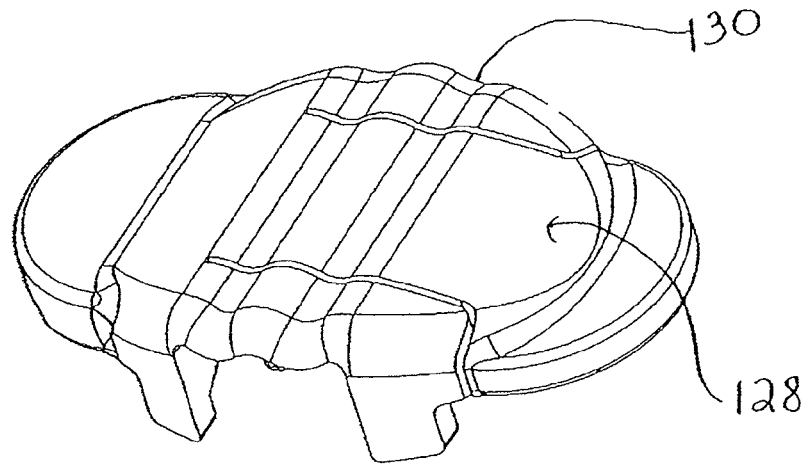
FIG. 16 is a top perspective view of the cover of another embodiment of a securing device.

The securing device 90 shown in FIGS. 10-15 operates in much the same way as the securing device 20, shown in FIGS. 1-9 and described above. Additionally, as cover 98 closes onto a catheter fitting 116 (or other catheter fittings of various sizes) which is positioned between the locating elements and latches onto base 96, locating pegs 100a may align with and engage locating pegs 100 as shown in FIGS. 14-15. This helps prevent cover 98 from shifting or moving, making the latching mechanism between latching elements 52 and latch holes 70 even more reliable. Also, spikes 106 and 106a are configured and arranged similar to the spikes in the embodiments of FIGS. 1-9 and described above. Thus, spikes 106 and 106a help compress and grip catheter fittings of various shapes and sizes such as catheter fitting 32, (e.g., by compressing the body and/or wings of the catheter fitting) securely holding the catheter fitting 32 in place and preventing substantial movement of the fitting in various dimensions as described above with respect to FIGS. 1-9.

Figure 17:
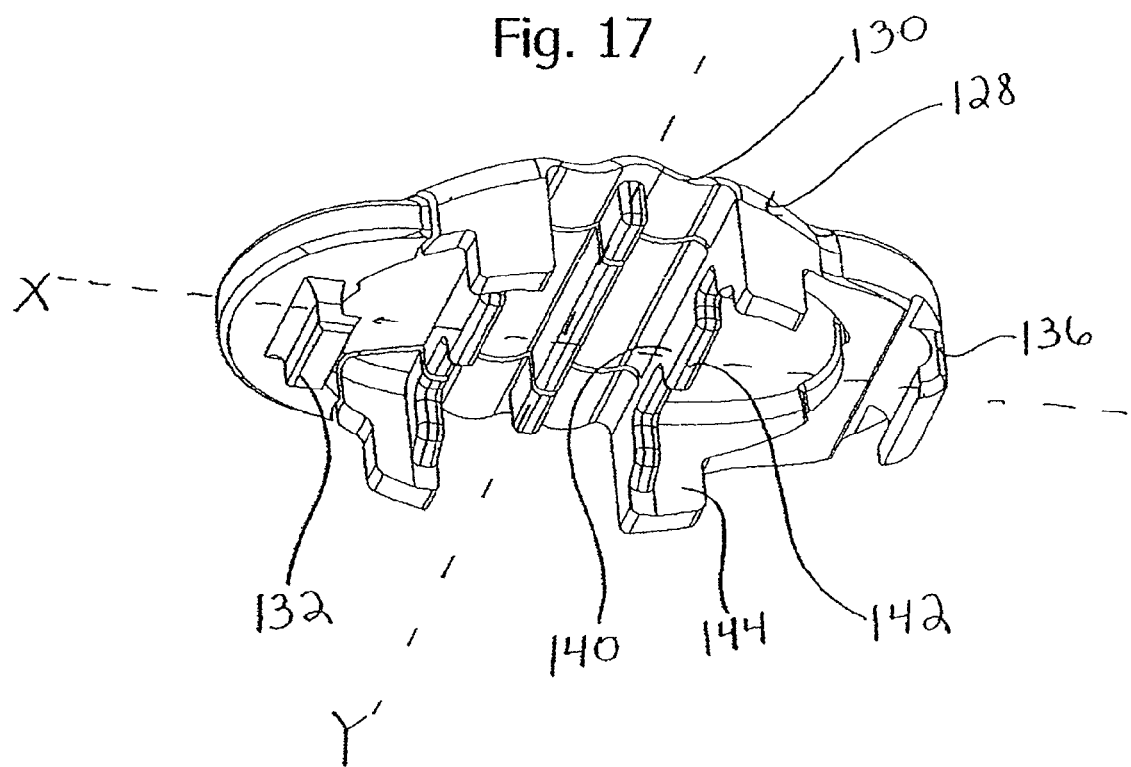
FIG. 17 is a perspective view of the under side of the cover shown in FIG. 16.
Figure 18:
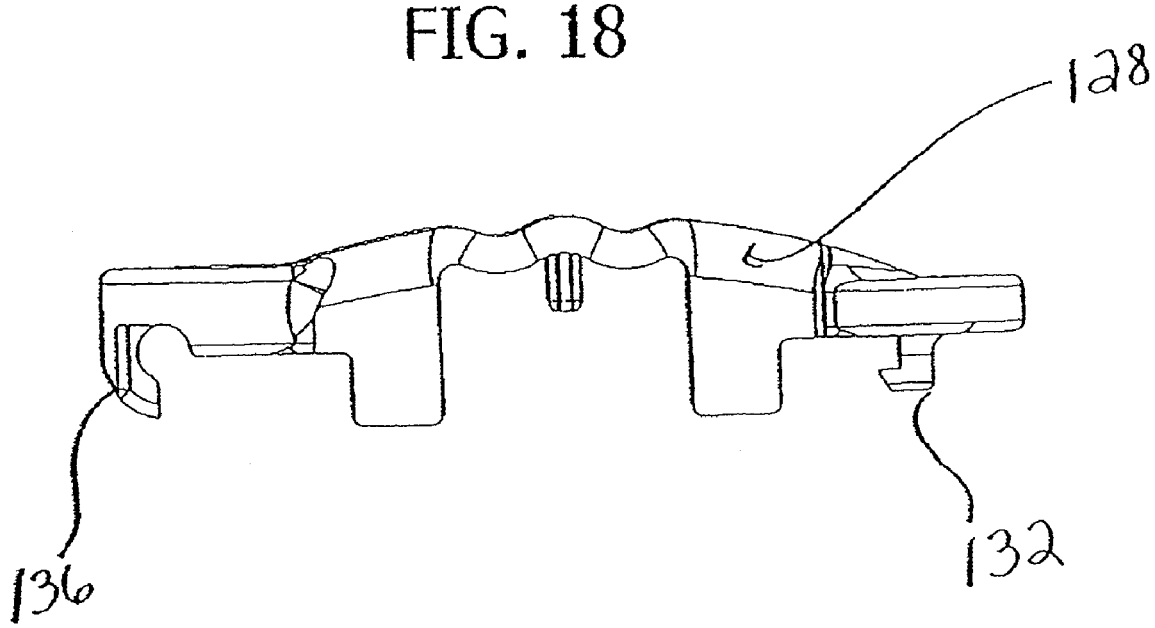
FIG. 18 is a side view of the cover shown in FIG. 16.

Another embodiment of a securing device 124 is shown in FIGS. 16-20. As best shown in FIG. 17, grooves 130 are provided on cover 128 which help make the cover more flexible. A latch 132 and snap hinge 136 are centered at opposite sides of the cover 128, along the lateral X axis of the cover 128. Web sections 140 run generally parallel to a longitudinal Y axis between column legs 144 and between grooves 130 on the under side of the cover 128. The web sections 140 include a capture element 142 and elevated ends 145 extending from the web sections 140.

Figure 19:
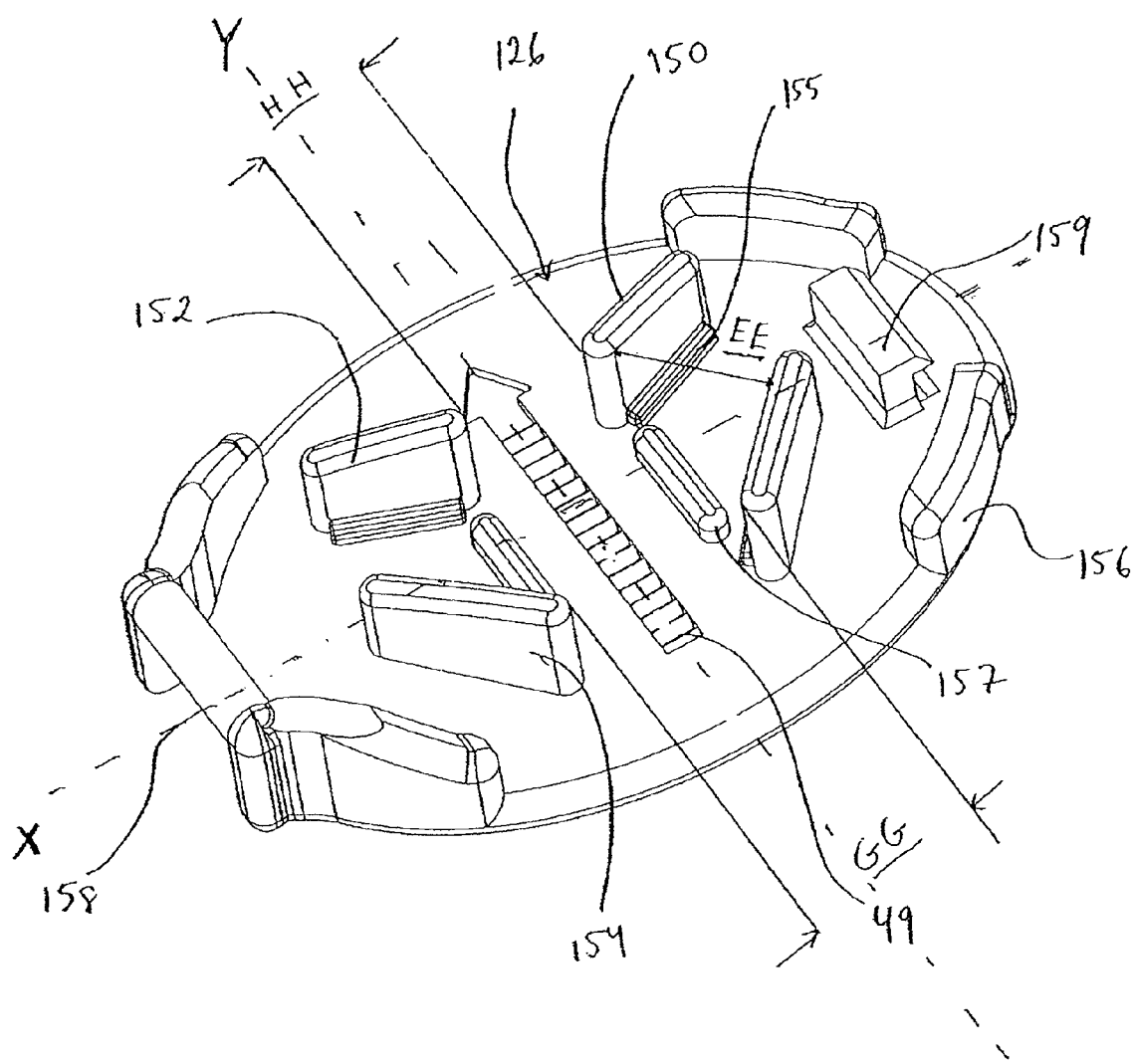
FIG. 19 is a top perspective view of a base for attachment to the cover of FIGS. 16-18.

As shown in FIG. 19, the device 124 may also include a base 126. The locating elements 150 on the base 126 include a front pair 152 and a back pair 154 of locating elements arranged in a front to back direction as indicated by arrow 49. In general, the locating elements 150 may be substantially symmetrical side-to-side about the longitudinal axis or centerline Y. The locating elements 150 help restrain a catheter and catheter fitting of various shapes and sizes and help prevent substantial side-to-side, back-to-front, axial and rotational movement of such catheters and catheter fittings on the base 126. At the foot of a locating element 150 is a ridge 155 and positioned in between the front pair 152 and back pair 154 of locating elements is a bar 157 running on either side of the arrow 49 and generally parallel to arrow 49. A bottom latch 159 and snap hinge base 158 are centered at opposite sides of the base 126, along the lateral X axis of the base 126. Side walls 156 may extend up form the base along the perimeter of the base 126.

In one embodiment the locating elements 150 are arranged such that a front locating element 152 is separated from a back locating element 154 by a dimension EE which extends from the inner tip of 152 straight back and perpendicular to 154. Also, the inner edge of the first or right back locating element 154 may be separated from the inner edge of the second or left back locating element 154 by a dimension GG running generally parallel to a lateral axis X. Also, the inner edge of the first or right front locating element 152 may be separated from the inner edge of the second or left front locating element 152 by a dimension HH running parallel to dimension GG. In one embodiment, dimension GG may be greater than dimension HH. In another embodiment dimension GG may be about 130 to 170% of dimension HH or more preferably about 140 to 160% of dimension HH.

Figure 20:
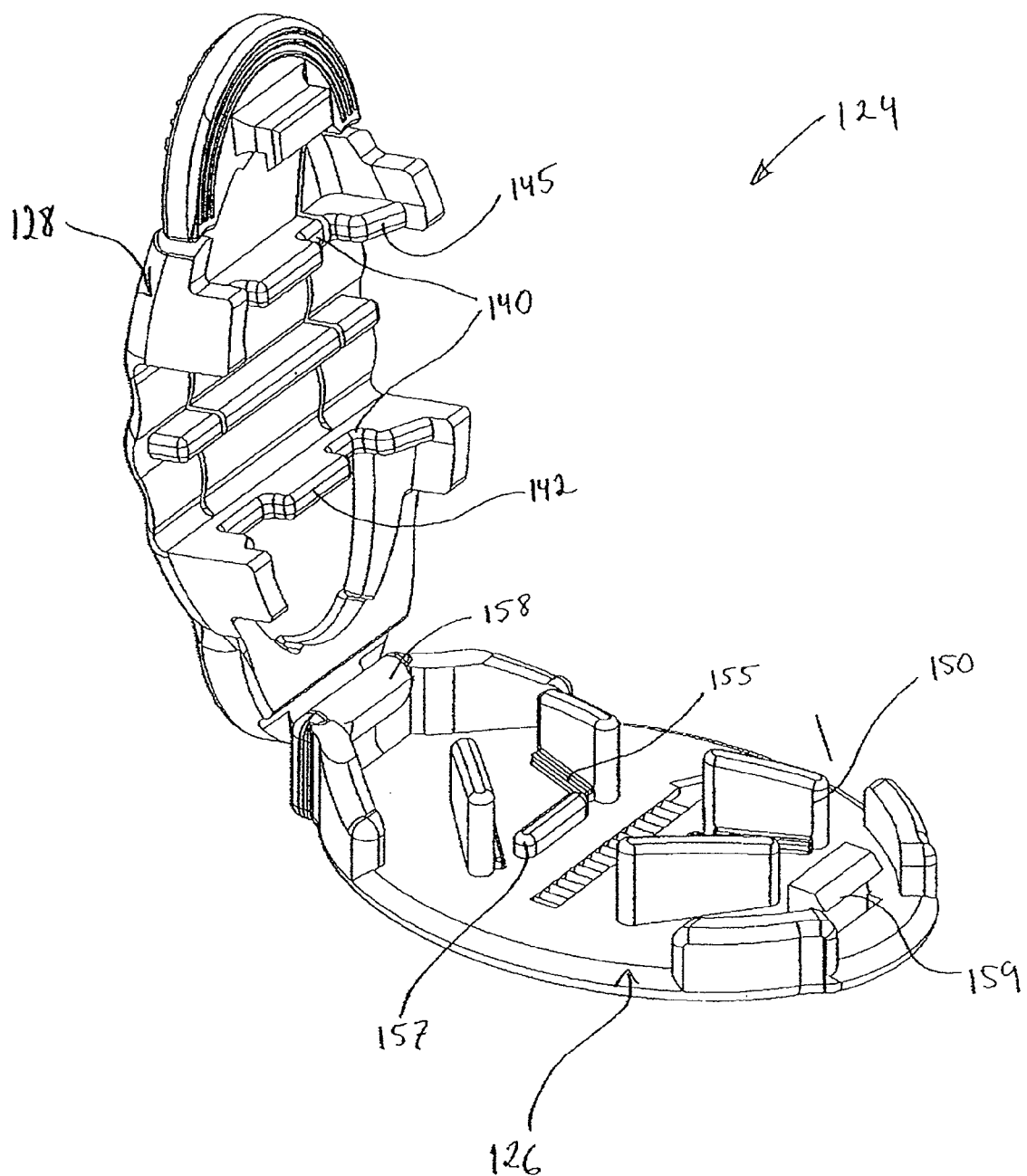
FIG. 20 is a top and front perspective view of the cover and base shown in FIGS. 16-19 fastened together to form a securing device.

As shown in FIG. 20, the device 124 operates such that the cover 128 is attached by the snap hinge 136 to the snap hinge base 158 of base 126 and the cover 128 can rotate down onto the base 126 into a closed position where the latch 132 and bottom latch 159 engage. In a closed position the capture element 142 on the web sections 140 is adapted to contact and compress the top of a catheter fitting held within device 124. The capture elements 142 help compress and grip catheter fittings of various shapes and sizes (e.g., by compressing the body and/or wings of a catheter fitting) securely holding the catheter fitting in place and preventing substantial movement of the catheter fitting such as in an axial, side-to-side, back-to-front, up and down and rotational direction. The capture elements may compress the catheter fitting against the ridge 155 and/or bar 157. The ends 145 of the web sections 140 serve a similar function as the locating elements discussed above as they also help restrain a catheter fitting and help prevent substantial side-to-side, back-to-front, axial and rotational movement of the catheter fitting. The web sections 140 including capture elements 142 and ends 145, as well as bars 157 and ridges 155, may be solid or spring molded and may be made of various materials as discussed above. Optionally, a base with no locating elements may be used with the cover 128 for compressing and holding a catheter.

Figure 21:
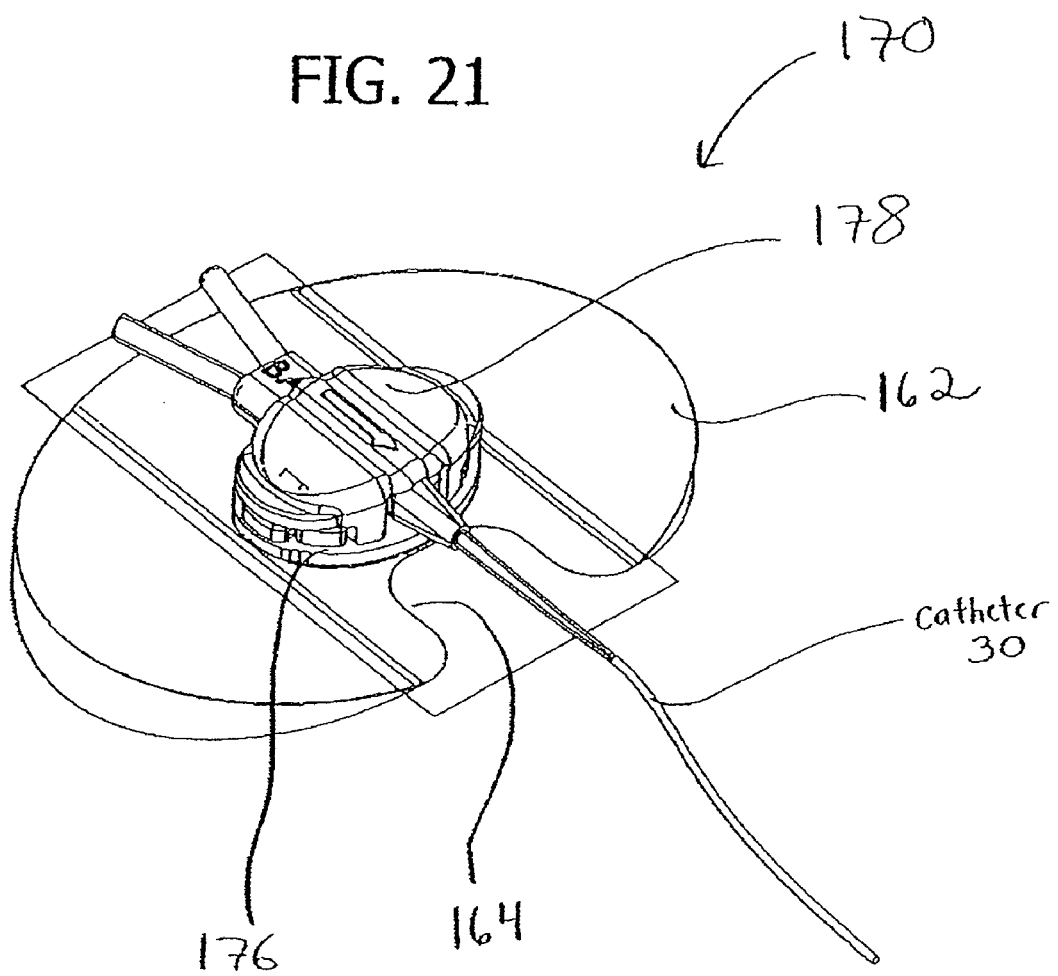
FIG. 21 is a top and front perspective view of a securing device attached to a pad.
Figure 22:
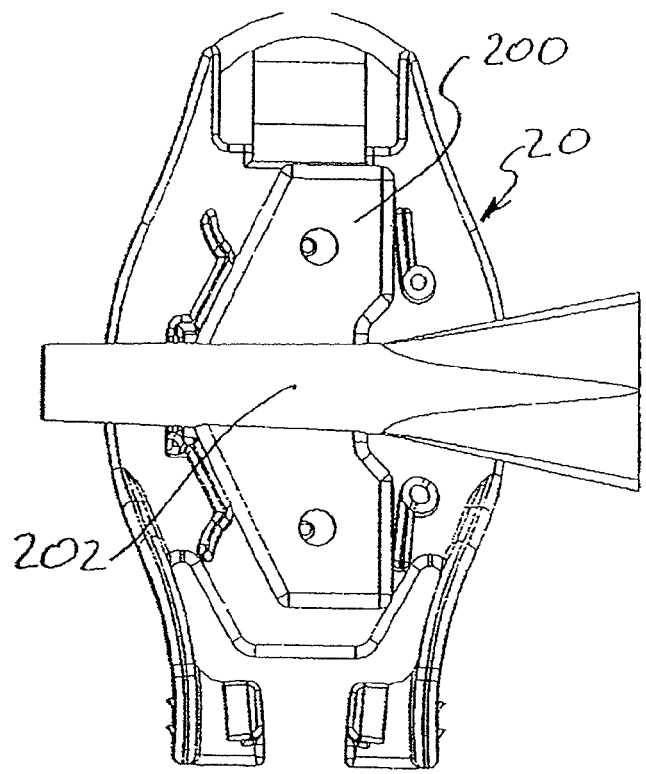

FIG. 21 shows securing device 170 having a base 176 and cover 178. The device is attached to an adhesive pad 162. This embodiment operates much like the embodiments of FIGS. 16-20 described above for securing catheters and catheter fittings having various shapes and sizes. The base 176 and cover 178 may snap fit together with or without a hinge feature.

Figure 23:
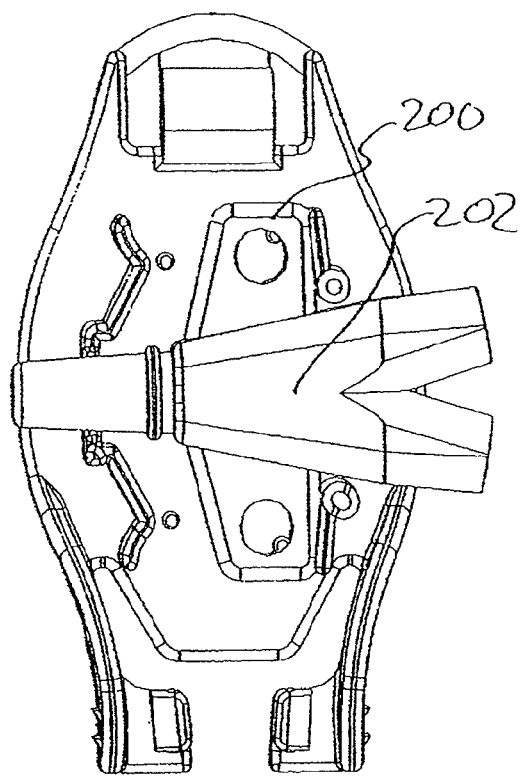
Figure 26:
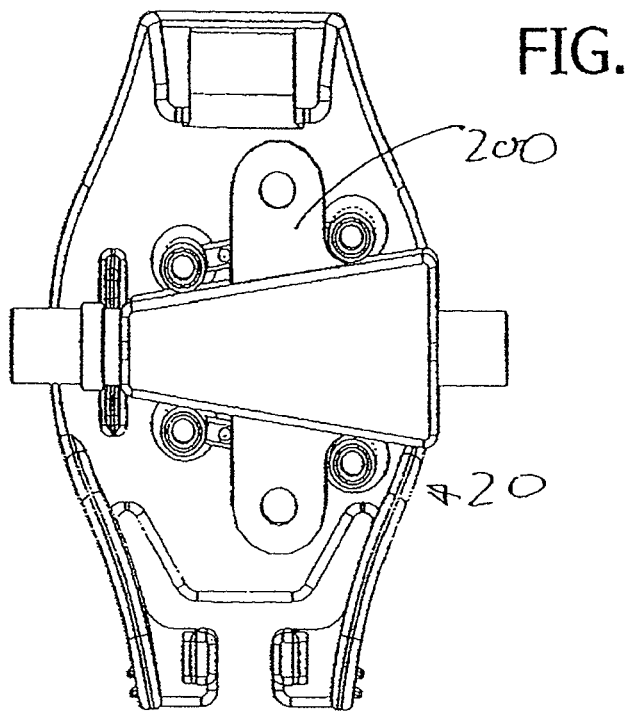
Figure 27:
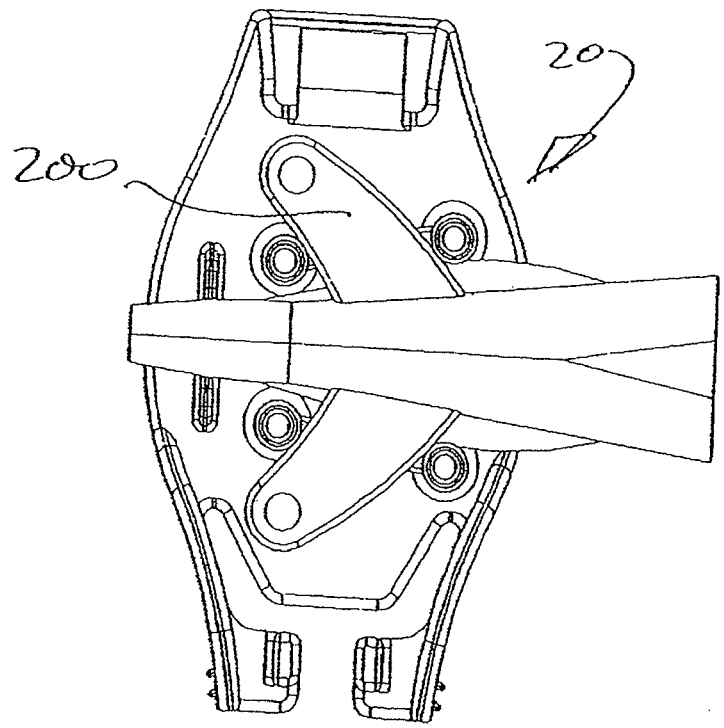
Figure 28:
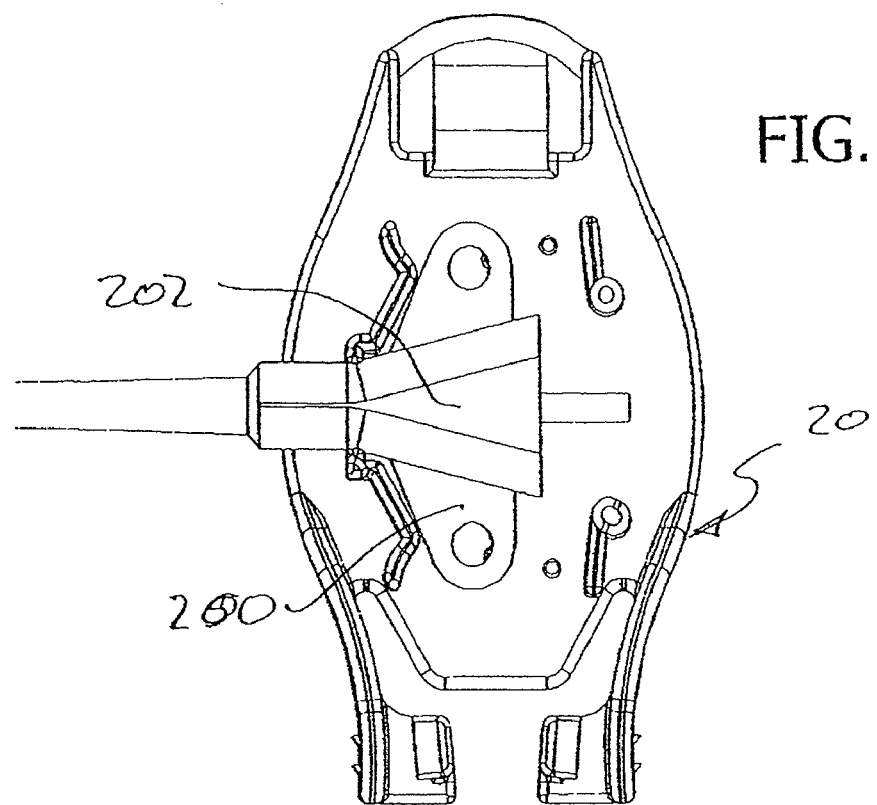
Figure 29:
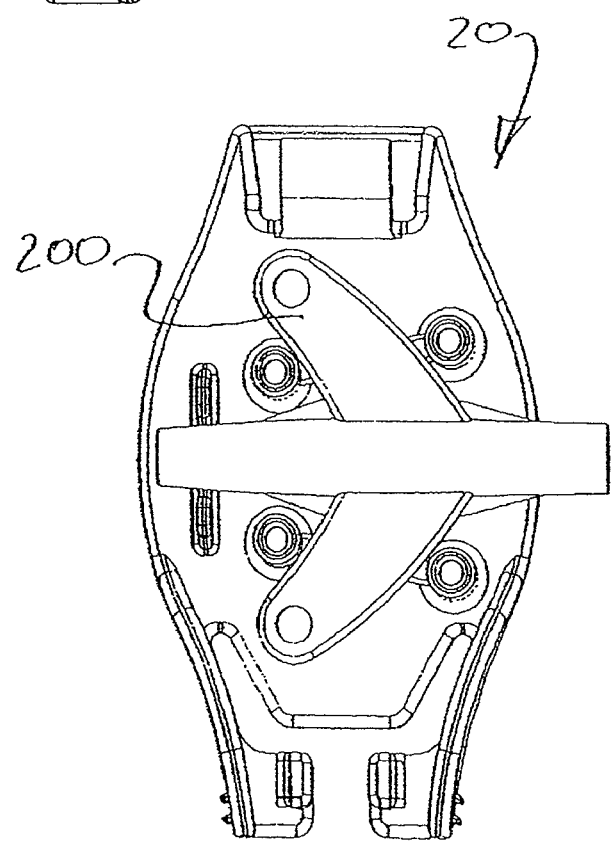

FIGS. 22-29 show the universal catheter securement device 20 in use with various different types of catheters. With some catheters, as shown in FIGS. 22, 24, 27 and 29, the wings 200 of the catheter 32 are restrained against virtually any longitudinal movement by the front and rear locating elements. With other catheters, such as shown in FIGS. 23, 26 and 28, the wings 200 of the catheter are narrower or smaller, leaving a gap between the locating elements. This would nominally allow the catheter to shift longitudinally under force (e.g., with pulling on the catheter tubes). However, when the cover is closed, the catheter body 202 and/or the wings are clamped tightly by the capture elements. This largely prevents any extensive inadvertent and undesirable movement of the catheter, even though there may be no direct physical contact with a front or rear locating element.

Figure 30:
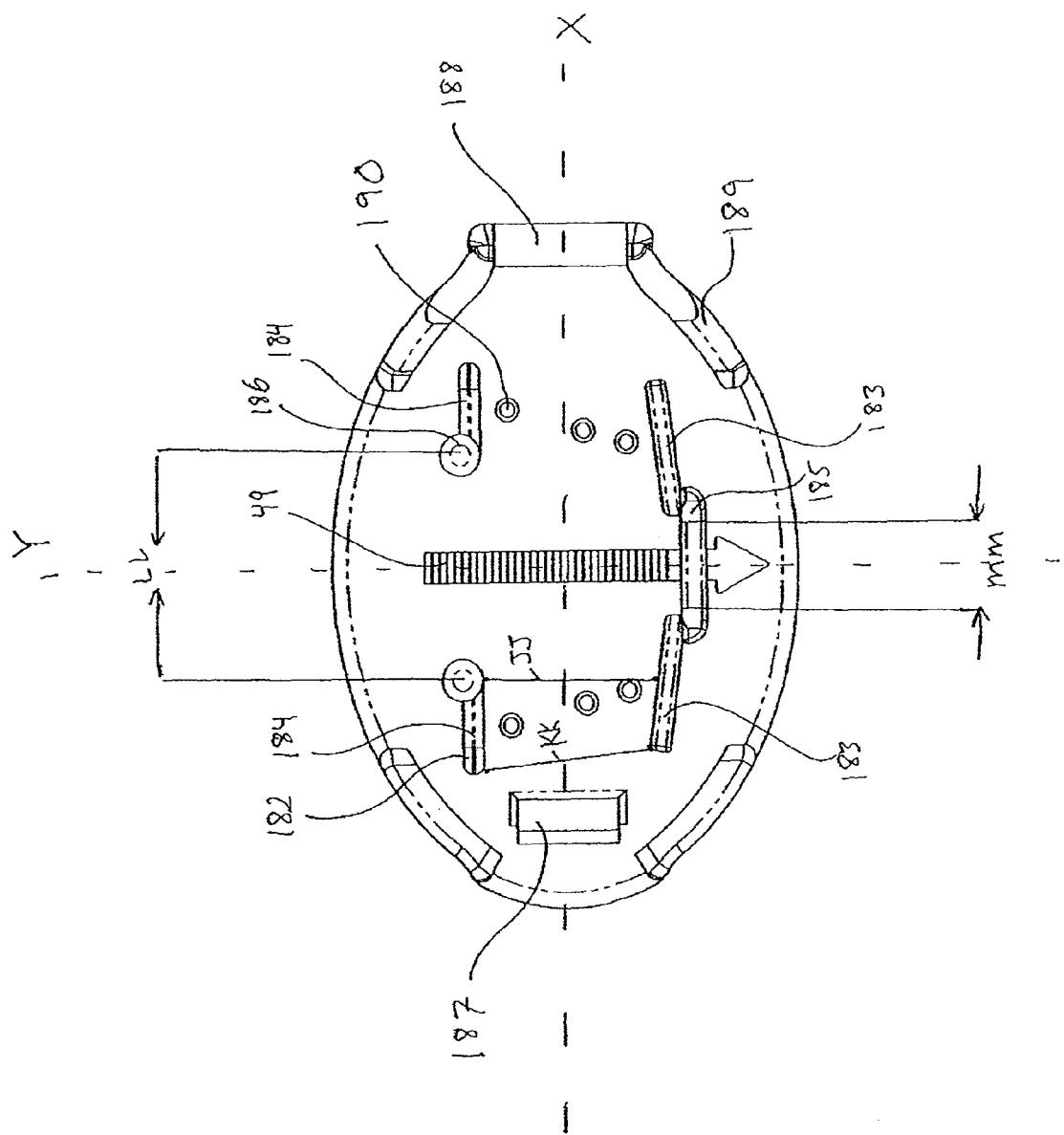
FIG. 30 is a top plan view of another base for use in a securing device.

FIG. 30 shows an alternative embodiment of a base 180 for use in a securing device. The locating elements 182 on the base 180 include at least one front wall 183 and a pair of back walls 184 arranged in a front to back direction as indicated by arrow 49. In general, the locating elements 182 may be substantially symmetrical side-to-side about the longitudinal axis or centerline Y and they are arranged to position and hold catheter and catheter fittings of various shapes and sizes to prevent substantial movement of such catheters and catheter fittings in various dimensions. The front wall 183 may be angled and a semicircular trough 185 may be positioned slightly forward of the front wall 183 and may be connected to the front wall. The back wall 184 is connected to a post 186. A bottom latch 187 and snap hinge base 188 are centered at opposite sides of the base 180, along the lateral X axis of the base 180. The base 180 may snap fit to a cover with or without a hinge feature. Side walls 189 may extend up form the base along the perimeter of the base 180 and spikes 190 may extend up from the base and run in a line on either side of arrow 49, between a front wall 183 and back wall 184. The base 180 can operate in conjunction with a cover in a manner to compress and/or restrain catheters and/or catheter fittings of various shapes and sizes and prevent their substantial movement in various dimensions.

In one embodiment the locating elements 182 are arranged such that a front wall 183 is separated from a back wall 184 by a dimension JJ which extends from a mid-point on an inner surface of the front wall 183, straight back and generally parallel to the longitudinal axis Y, to the post 186. A front wall 183 may also be separated from a back wall 184 by a dimension KK which extends from the outer edge of the front wall 183 to the outer edge of the back wall 184. Also, a first or right post 186 may be separated from a second or left post 186 by a dimension LL running generally parallel to a lateral axis X. Further, a semicircular trough 185 may have a dimension MM running generally parallel to dimension LL. In one embodiment, dimension JJ is greater than dimension KK. In one embodiment, dimension LL is greater than dimension MM. In another embodiment dimension JJ may measure about 0.33 to 0.37 inches, preferably 0.34 to 0.36 inches, or more preferably 0.35 inches in length and dimension KK may measure about 0.31 to 0.35 inches, preferably 0.32 to 0.34 inches, or more preferably 0.33 inches in length. Also, dimension LL may measure about 0.41 to 0.45 inches, preferably 0.42 to 0.44 inches, or more preferably 0.43 inches in length and dimension MM may be about 0.15 to 0.19 inches, preferably 0.16 to 0.18 inches, or more preferably 0.17 inches in length.

In an alternative design, the device may use a generally plane cover and base, with the device not having locating elements 40 and/or spikes 48. In this design, the cover and base act as simple clamping elements to secure the catheter. With sufficient clamping force applied, the cover and base can restrain the catheter against significant movement, without using locating elements, such as walls, posts, etc. Force multiplying elements, such as levers, cams, screw threads, etc. may be used in this type of design to provide adequate clamping force.

The above securing devices may be molded plastic or made of other materials suitable for use with patients. Any of the bases or covers described may be provided in the shapes shown or in other shapes as well, including irregular shapes. Outer walls extending up from a base around the outside of the locating elements may also be provided to help align and engage a cover onto a base. Also, the various embodiments of securing devices described above may be attached to a patient in a variety of ways, e.g., with a pad as shown in FIG. 2, or with other adhesive means.

In other embodiments, a securing device for holding catheters and the like in place advantageously has two parts. A base attached to a pad forms one part. A cover is the other part. The cover may optionally be tethered to the base. The pad preferably has an adhesive back surface for attaching the pad to the patient's skin. The base on the pad has positioning elements such as walls or surfaces adapted to fit securely around a catheter fitting. The catheter fitting may be placed into or onto the base from above. The positioning elements prevent any substantial movement of the catheter fitting, in two dimensions, relative to the base or pad, e.g. in the front/back and left/right side directions. The cover is attached to the base over the catheter fitting. One or both of the base and cover have latching elements for holding the cover onto the base. The cover prevents movement of the catheter fitting in a third dimension, i.e., vertically up and out of the base. Consequently, after the cover is attached to the base over the catheter fitting, the catheter fitting and the catheter are securely held in place on the patient. The catheter may be released and removed from the base by temporarily disengaging the latching elements. The latching elements may be disengaged by, for example, squeezing the sides of the cover. The catheter can therefore be quickly and easily attached to or removed from the patient. Such devices may be used with, e.g., PICC lines, IV catheters, Foley catheters, heart catheters, J-loops, and various other catheters, as well as tubes, cables, lines, and other medical devices.

Figure 31:
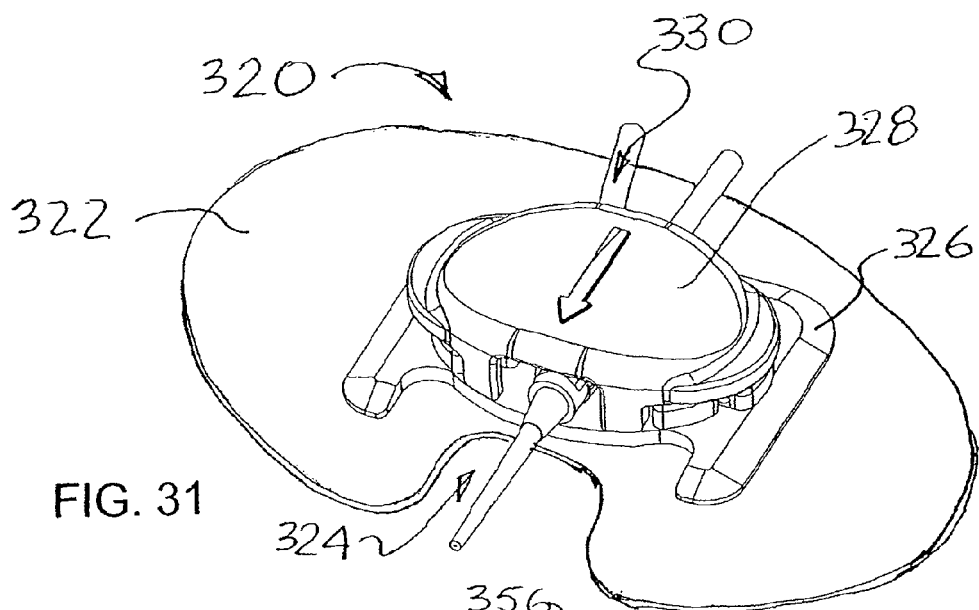
FIG. 31 is a top and front perspective view of another embodiment of a securing device. The pad shown in FIG. 31 is used on each of the various securing devices described below. However, the pad as shown in FIG. 31 is omitted from the remaining drawings, to allow for better illustration of the other components.

For example, FIG. 31 shows an embodiment of a securing device 320 having a base 326 attached to a pad 322. The pad 322 is flexible to conform to the patient's arm or other site. The back side of the pad 322 preferably has one or more peelable strips over an adhesive layer or surface. The specific pad shape and size is not essential and various alternatives may be used. In the example shown in FIG. 31, the pad 322 generally is oval or round, and with a major diameter of from about 1-6, 2-5 or 3-4 inches. The pad does not need any suture holes.

As shown in FIGS. 31-34, a base is attached onto the top side of the pad 322 at a generally central location. The base 326 has positioning walls 350 shaped and dimensioned to fit securely around a fitting 332 on a catheter 330. For the catheter 330 shown in FIGS. 32 and 33, four separate positioning walls 350 are used. In this case, the catheter walls 350 are adapted to fit around the curved ends of the fitting plate. The walls 350 are spaced apart in the back to front direction (indicated by the arrow 356 in FIG. 32) by a dimension just nominally greater than the width of the fitting plate 334. Similarly, the walls 350 are spaced apart side to side by a dimension nominally greater than the length of the fitting plate.

Figure 32:
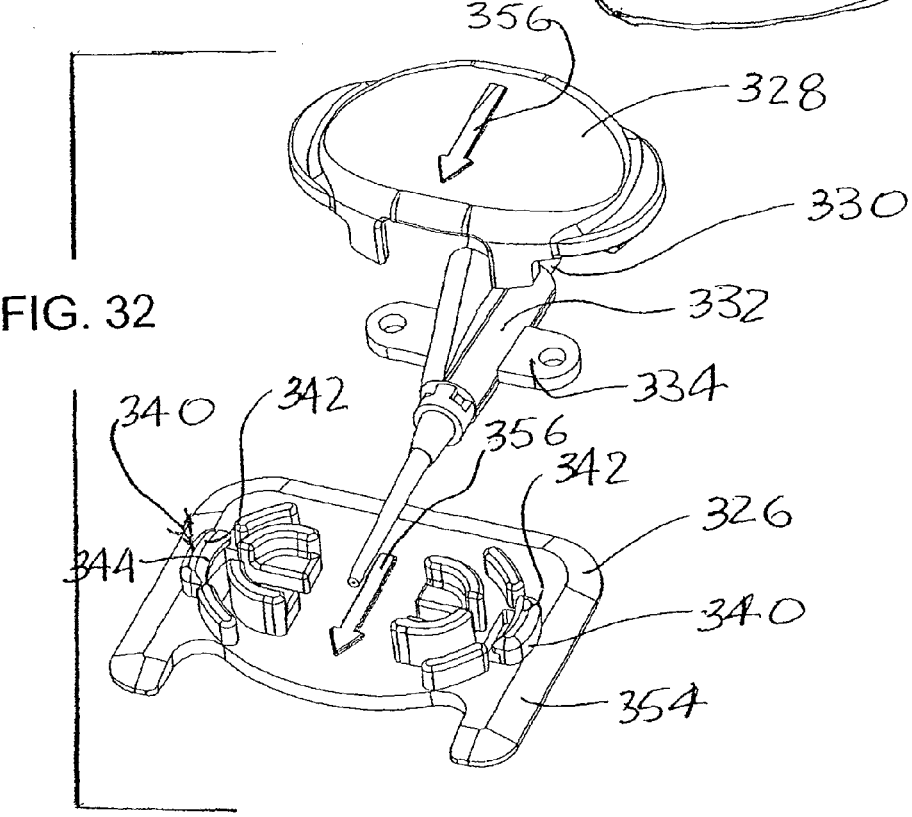
FIG. 32 is an exploded perspective view of the device shown in FIG. 31.
Figure 33:
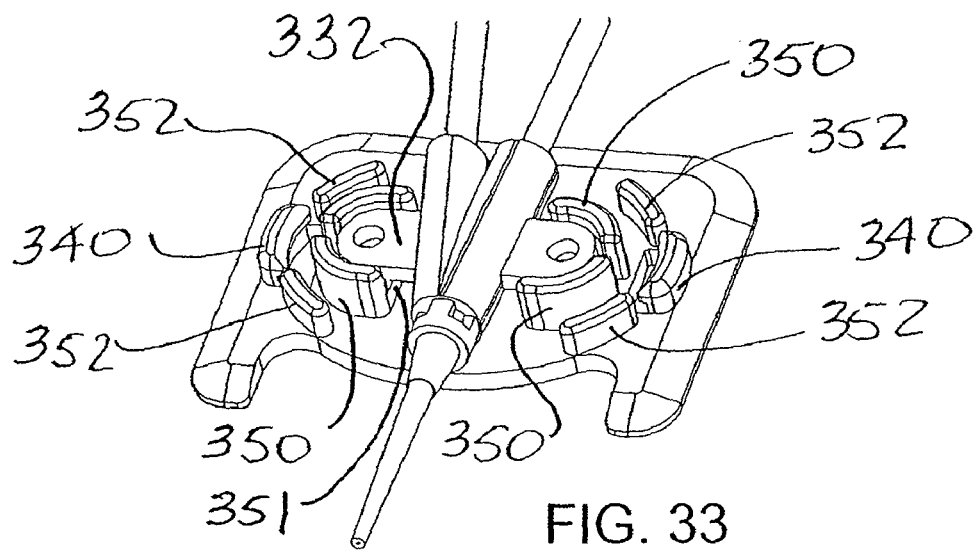
FIG. 33 is a top perspective view of the device shown in FIG. 31, with the cover removed.
Figure 34:
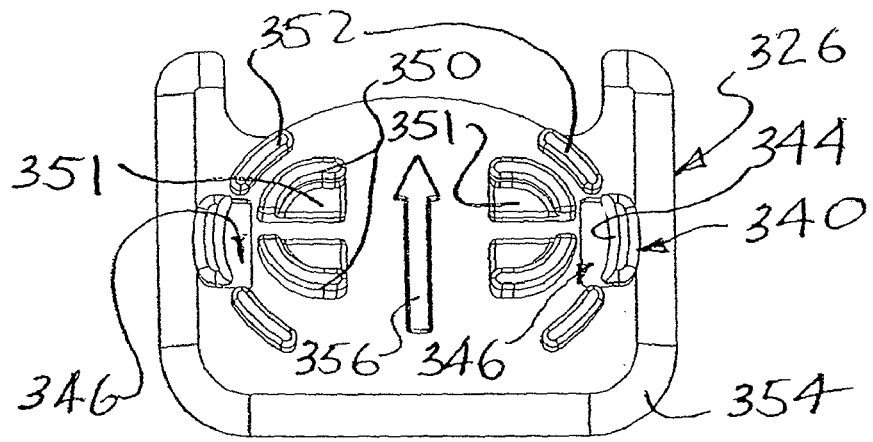
FIG. 34 is a plan view of the base shown in FIGS. 32 and 33.

Referring to FIGS. 32-34, outer walls 352 extend up from the base 326 around the outside of the positioning walls 350. The outer walls are lower than the positioning walls. Latching arms 340 extend up generally from opposite sides of the base 326. An angled face or surface 344 is provided at the top or head 342 of each of the arms 340. The base 326 may have a tapered or inclined edge or rim 354. One or more through holes 346 may be provided in the base 326, if desired, for manufacturing purposes. An arrow symbol 356 may be provided on the base 326 and/or the cover 328, to indicate how the catheter 330 should be installed into the device 320.

Figure 35:
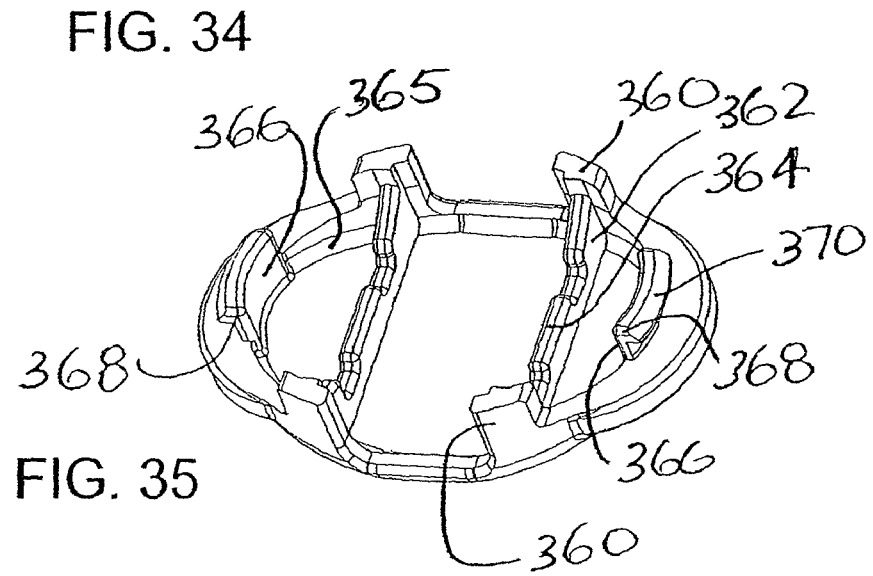
FIG. 35 is a perspective view of the under side of the cover shown in FIGS. 31 and 32.

As shown in FIGS. 32 and 35, the cover 328 has latching arms 366, with an angled surface or face 370 at the outer or lower end 368 of each arm 366, similar to the latching arms 340 on the base 326. In the oblong cover 328 shown in FIG. 35, the arms 366 are centered at opposite sides of the cover, along the major axis of the cover. Web sections 362 run between column legs 360 on the bottom or under side of the cover 328. The column legs extend out beyond the latching arms 366. A contact or land surface or area 364 on the web sections 362 are adapted to lightly contact the top of the catheter fitting 332 when the cover 328 is attached to the base 326.

In use, after the catheter has been placed, the skin at the securement site is preferably cleaned. The catheter fitting 332 is then placed into or onto the base 326, as shown in FIG. 33. Land or boss areas 351 may be provided on the floor of the base 326, within the positioning walls 350, as shown in FIGS. 33 and 33. These areas 351 may be used, if desired, to support the catheter fitting 332 off of the floor of the base 326. The cover 328 is then attached to the base 326 over the fitting 332, as shown in FIG. 31. The outer walls 352 may align with and engage against inner rim surfaces 365 on the cover 328, as shown in FIG. 35. This interaction, if used, helps to align the cover onto the base, and to securely attach the cover to the base. The column legs rest on flat outer areas of the base.

The column legs 360 are dimensioned so that when they bottom out on the base 326, the contact surfaces 364 rest on the catheter fitting 332. The legs 360 prevent crushing or deformation of the catheter fitting, by keeping the contact surfaces 364 at a specified dimension above the base floor. As a result, the catheter fitting cannot be crushed, even if the cover is forcefully clamped down onto the base. The fitting 332 is securely held in place (horizontally) on the base between the positioning walls and is held in place vertically between the floor of the base 326 and the contact surfaces 364 of the cover.

As the cover is moved down onto the base 326, the angled surfaces 344 on the base latching arms 340 engage the angled surfaces 370 on the cover latching arms 366. This provides for a cover self aligning operation. The arms 340 and 366 are somewhat resilient and can flex slightly under load in the lateral direction. As a result, as the cover is moved into engagement with the base, the base latching arms 340 flex slightly outwardly, and the cover latching arms flex slightly inwardly. The surfaces 344 and 370 of the arms 340 and 366 slide against and then pass by each other. The arms 340 and 366 then flex back to near their original lateral positions, locking the cover 328 onto the base 326. The peel strip(s) are removed from the back of the pad 322, and the pad is placed onto the prepared securement site. The device 320 then prevents virtually any movement of the catheter fitting 332, which is joined to or part of the catheter 330. A cut out 324 may be provided at the front of the pad 322 to allow the base 326 to be closer to the incision or catheter entry point.

The catheter 330 may be removed by squeezing the sides of the cover 328 towards each other. The cover 328 is slightly flexible. Squeezing causes the cover to curve or bow up. As the cover curves, the arms 366 are drawn inwardly enough to pull the ends 368 of the arms 366 on the cover 328 away from the ends 342 of the arms 340 on the base 326. The head or ends 342 and 368 can then pass by each other as the cover is lifted off of the base.

Figure 36:
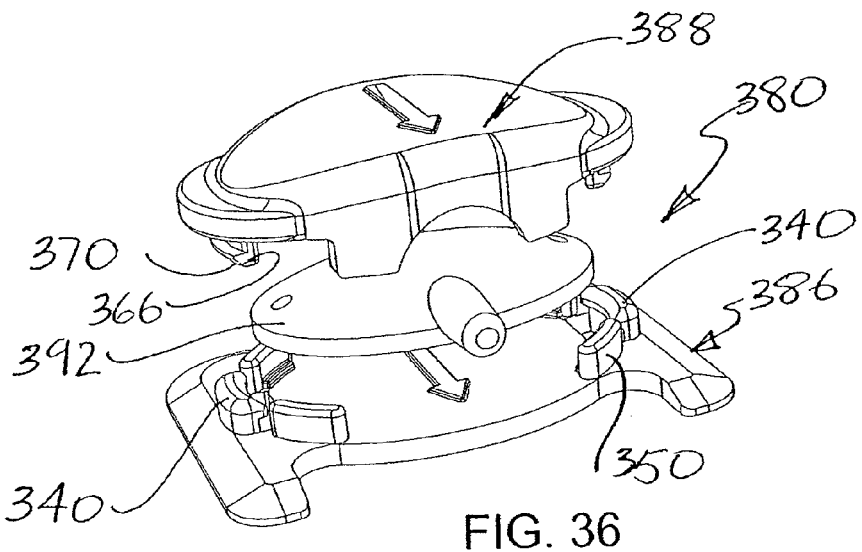
FIG. 36 is an exploded top and front perspective view of another securing device design useable with another type of catheter.
Figure 37:
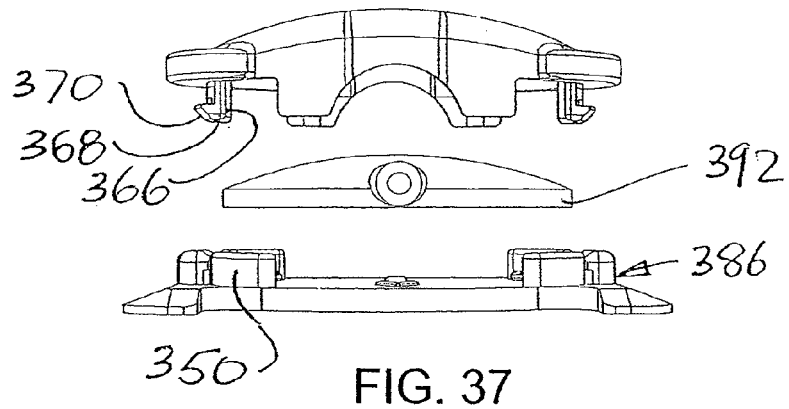
FIG. 37 is a front view of the device shown in FIG. 36.
Figure 38:
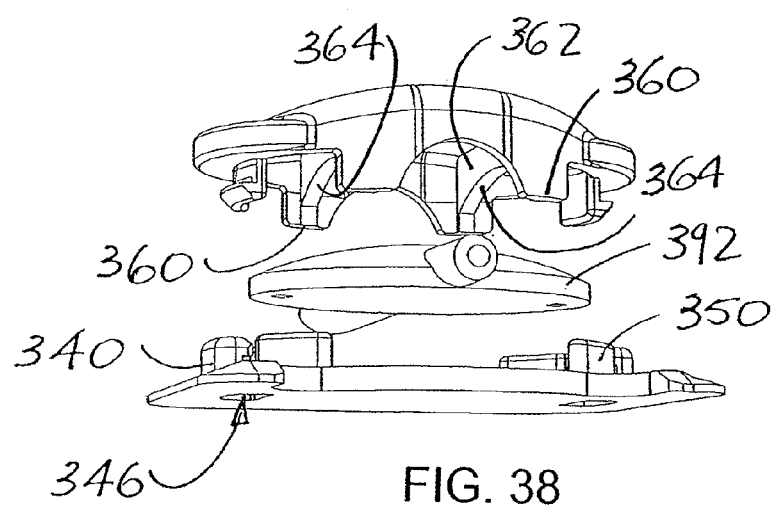
FIG. 38 is a front and bottom perspective view of the device shown in FIGS. 36 and 37.
Figure 39:
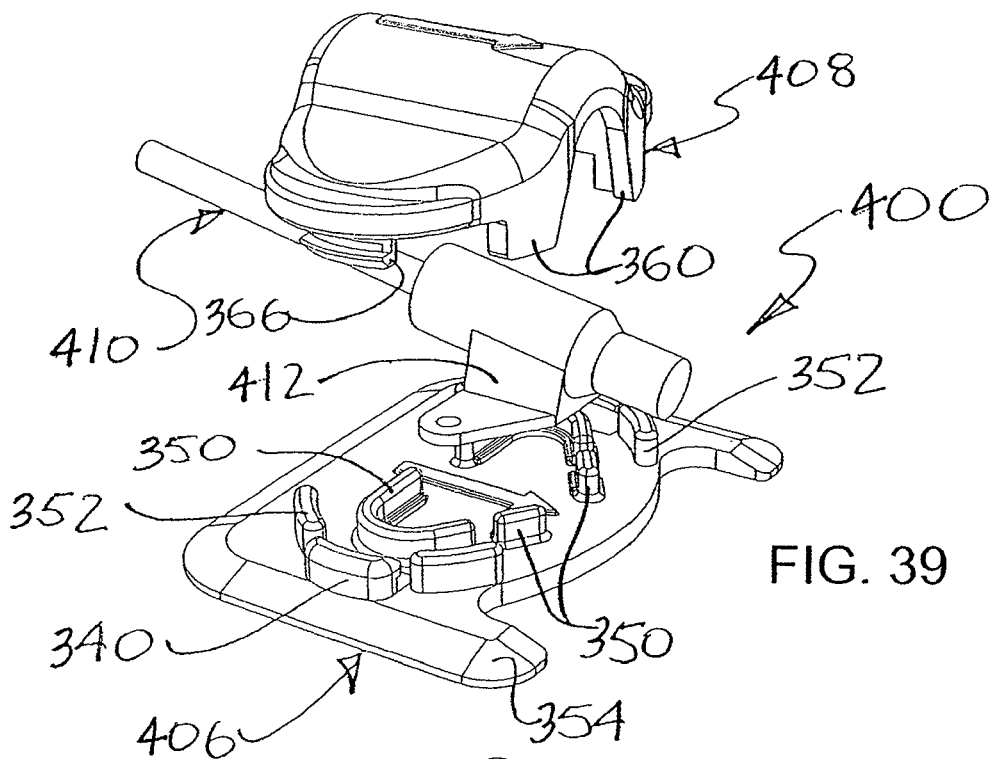
FIG. 39 is a top and side exploded perspective view of another securing device design useable with another type of catheter.

FIGS. 36-38 show another embodiment of a securing device 380 for use with a catheter 390 and catheter fitting 392. The cover 388 has curved contact surfaces 364 matching the top of the fitting 392. The base 386 has positioning walls 350 adapted to fit around the fitting 392.

Figure 40:
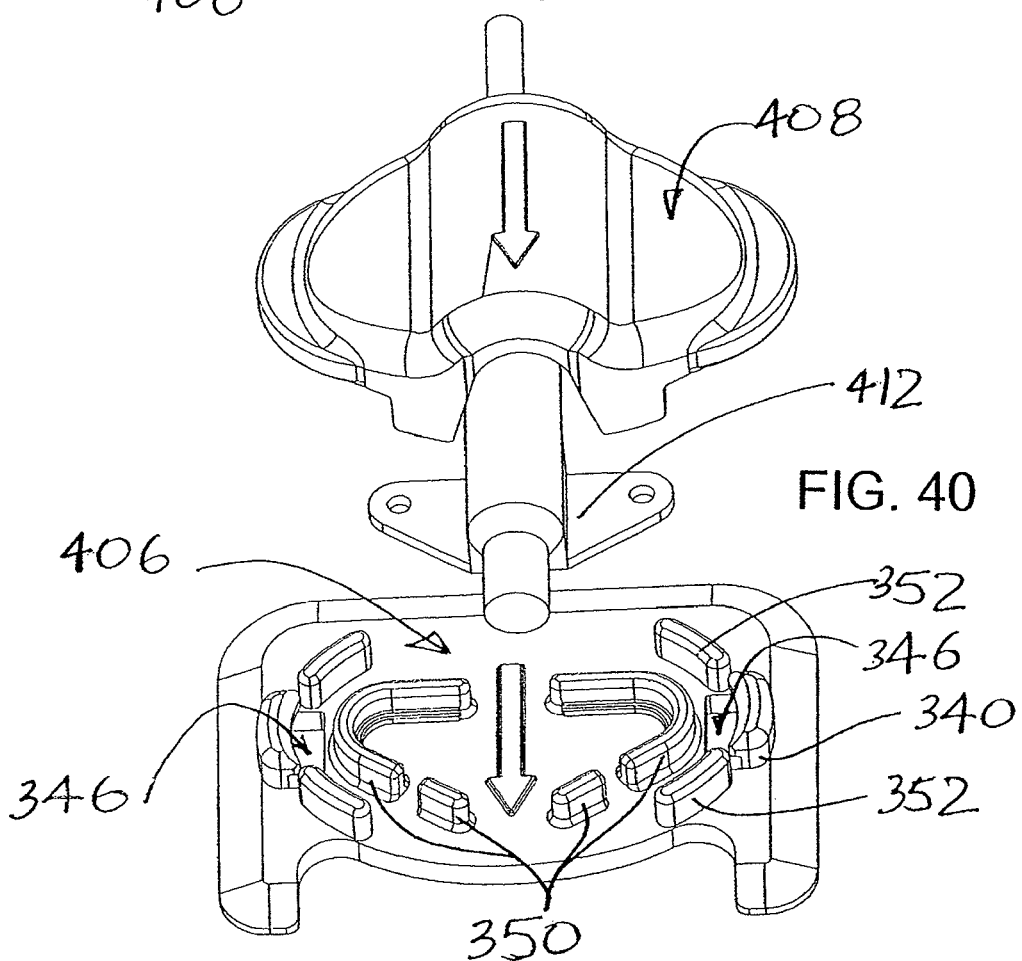
FIG. 40 is a top and front view of the device shown in FIG. 39.
Figure 41:
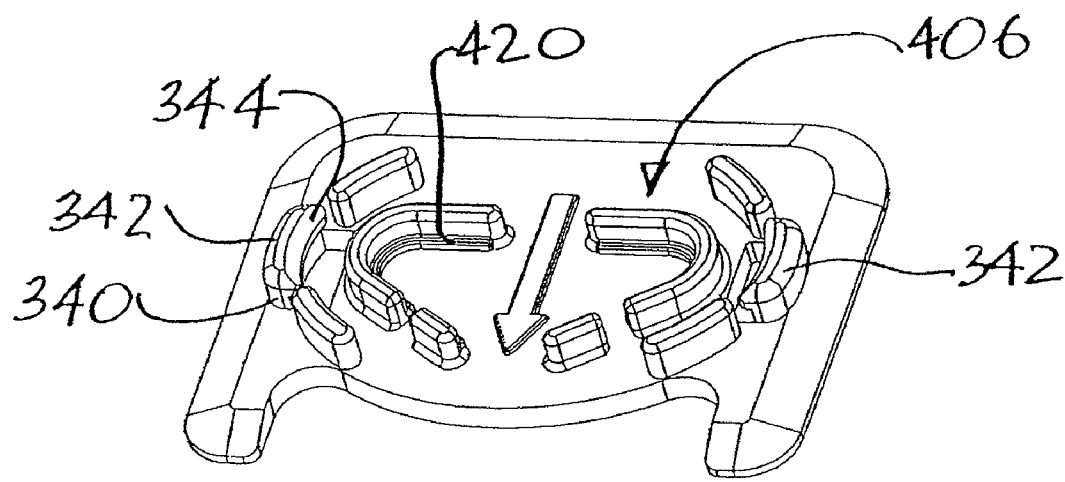
FIG. 41 is a top perspective view of the base shown in FIGS. 39 and 40.
Figure 42:
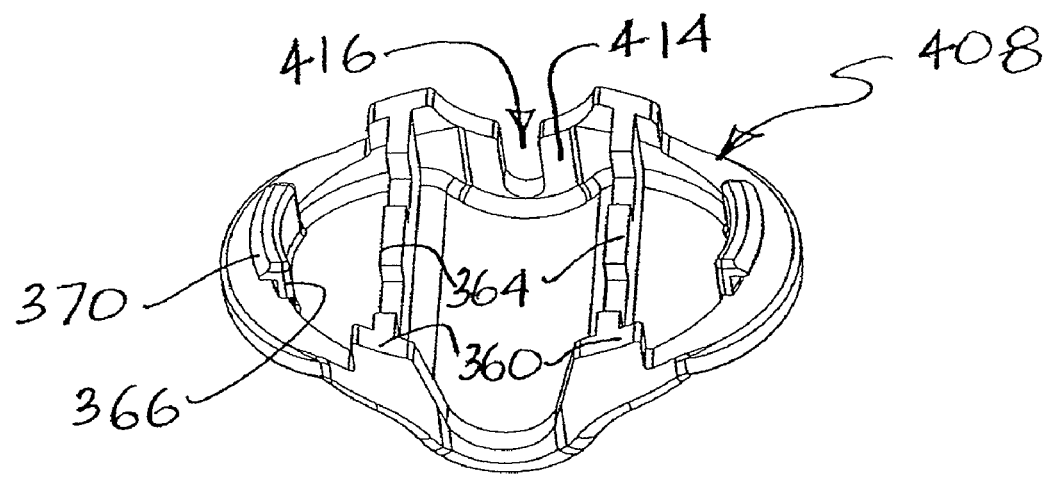
FIG. 42 is perspective view of the under side of the cover shown in FIGS. 39 and 40.

FIGS. 39-42 show another embodiment of a securing device 400 for use with another type of catheter 410 and catheter fitting 412. As shown in FIG. 40, the positioning walls 350 on the base 406 are segmented. The cover 408, as shown in FIG. 42, includes an opening 416 in a rear wall 414.

Figure 44:
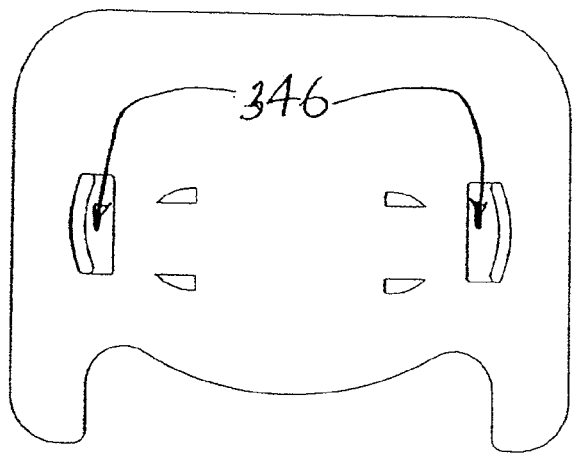
FIG. 44 is a bottom view of the base shown in FIG. 43.
Figure 43:
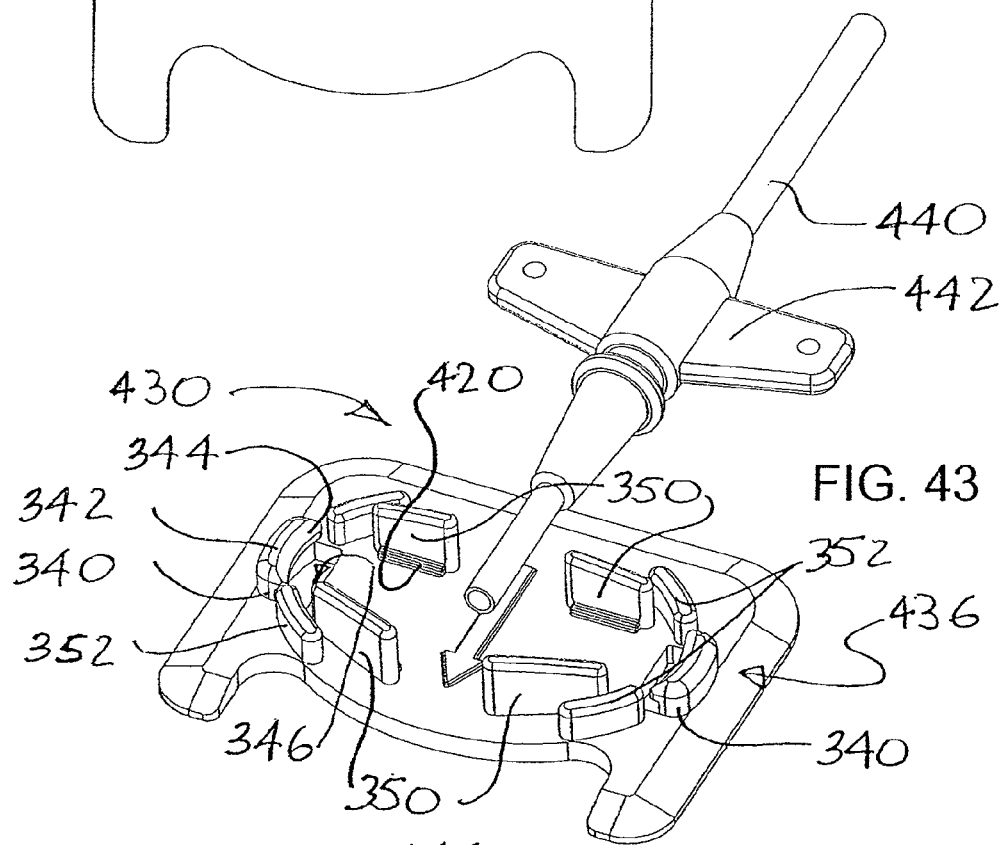
FIG. 43 is a top and side exploded perspective view of another securing device design useable with another type of catheter.
Figure 45:
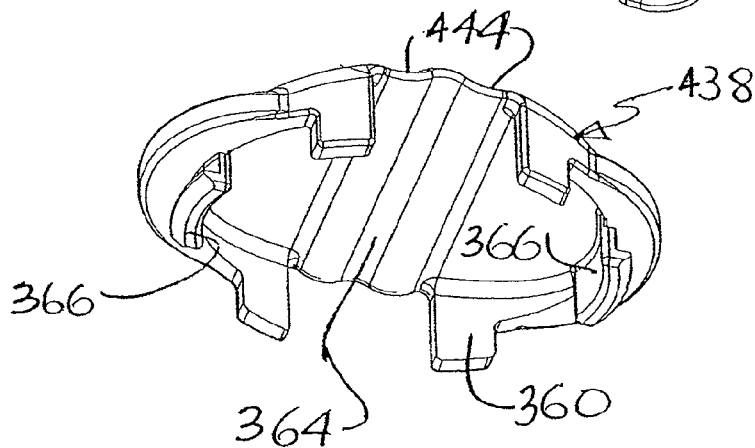
FIG. 45 is perspective view of the under side of the cover used with the base shown in FIG. 43.
Figure 46:
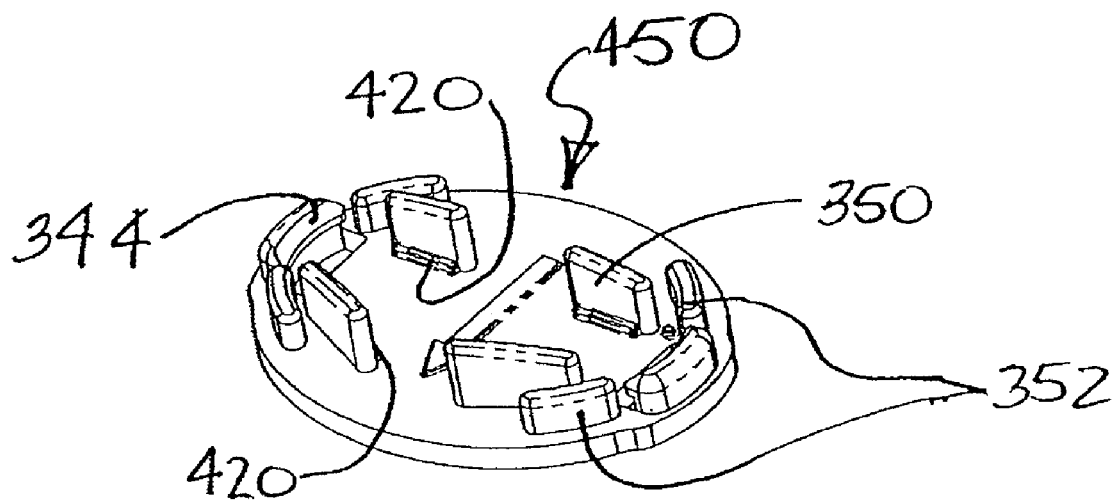
FIG. 46 is a perspective view of an alternative base, similar to the base shown in FIG. 43, and having a generally oval shape.
Figure 47:
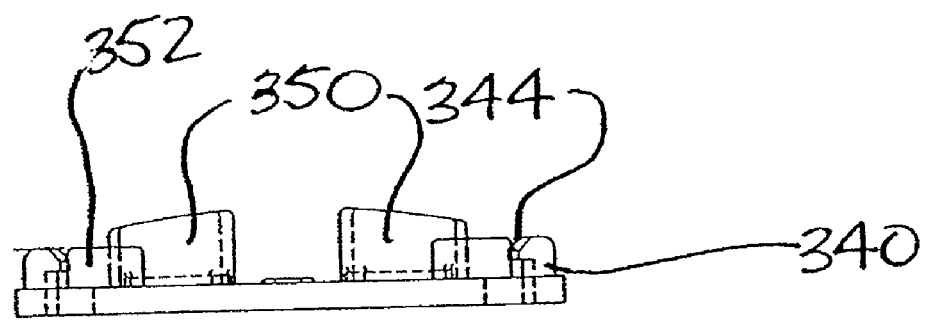
FIG. 47 is a side view of the base shown in FIG. 46.

FIGS. 43-45 show another embodiment of a securing device 430 for use with yet another type of catheter 440 and catheter fitting 442. In this design, four positioning walls 350 are provided on the base 436. Grooves 444 may be provided on the cover 444 to make the cover more flexible. As shown in FIGS. 41, 43 and 46, ramps or ridges 420 may be provided on the base floor near or adjoining one or more of the positioning walls 350. These features may be used to set the orientation of the catheter fitting in the device. FIGS. 46 and 47 show a base 450 similar to the base 436 shown in FIG. 43. The base 450 is generally oval shaped as opposed to the more rectangular base 436 shown in FIG. 43.

The devices shown in FIGS. 36-47 operate in the same way as the device 320 shown in FIGS. 31-35 and described above. The base and cover in each design may be molded plastic. The positioning walls 350 may be segmented, as shown in the drawings, or continuous. Indeed, a single continuous positioning wall surrounding the catheter fitting 442 on all sides may be used. Alternatively, multiple short spaced apart wall segments around two, three or more sides of the fitting may also be used. The wall segments may be various shapes, including generally rectangular, as shown in FIGS. 45-47, as well as round, square, hexagonal, etc. Positioning or locating elements, such as the walls 350, may optionally also be provided on the cover. Moveable or adjustable positioning elements or wall segments may also alternatively be provided on the base. If used, these may have a single direction or ratchet feature, so that they can move only inwardly to contact the sides of the catheter fitting. Moveable positioning elements may allow use of a single device with more than one specific type of catheter.

Thus novel devices and methods have been described. Various changes and modifications may of course be made without departing from the spirit and scope of the invention. The invention, therefore, should not be limited, except to the following claims, and their equivalents.

The invention claimed is:

1. An anchoring system for securing a catheter to the body of a patient, comprising:
   a fitting on a medical line, the fitting having a body and a pair of outwardly extending wings;
   a base member having two pairs of wall segments, the wall segments being disposed relative to the base member so as to generally define a land area therebetween for receiving the body of the fitting, the wall segments from each pair of wall segments being spaced apart to receive at least a portion of a wing of the catheter therebetween and to inhibit at least longitudinal movement of the secured wing relative to the base member;
   a trough extending up from the base member and positioned forward of the two pairs of wall segments, the trough receiving at least a portion of the body of the catheter;

a cover being attachable to the base member, the cover being movable to an engaged position in which at least a portion of each wall segment is disposed between the cover and the base member; and interengaging structure which releasably secures together the base member and the cover in the engaged position.

2. An anchoring system as in claim 1, wherein each pair of wall segments is disposed relative to the base member so as to contact the pair of outwardly extending wings.

3. An anchoring system as in claim 1, wherein each pair of wall segments is disposed relative to the base member so as to contact the cover when the cover is in the engaged position.

4. An anchoring system as in claim 1, wherein each pair of wall segments is arranged relative to the other pair of wall segments so as to define a non-uniform distance across said land area as measured in a longitudinal direction.

5. An anchoring system as in claim 1, wherein an upper surface of each pair of wall segments is spaced above the base member so that at least a portion of the body of the fitting lies between the base member and the upper surface at least when the catheter is secured in the retainer.

6. An anchoring system as in claim 1, wherein at least a portion each wall segment has a rectangular shape.

7. An anchoring system as in claim 1, wherein the interengaging structure comprises at least two securement members configured to interact with the cover when the cover is in the engaged position.

8. An anchoring system as in claim 7, wherein the cover includes at least two receptacles configured to interact with the at least two securement members when the cover is in the engaged position.

9. An anchoring system as in claim 8, wherein each receptacle receives a corresponding portion of the at least two securement members at least when the cover is in the engaged position.

10. An anchoring system as in claim 7, wherein each of the at least two securement members has an angled surface which locks to the cover when the cover is in the engaged position.

11. An anchoring system as in claim 8, wherein each of the at least two securement members has an enlarged head at an end distal of the base member.

12. An anchoring system as in claim 11, wherein each receptacle receives a corresponding one of the enlarged heads when the cover is in the engaged position.

13. An anchoring system as in claim 7, wherein the cover and each of the at least two securement members are configured to flex slightly when the cover is moved to the engaged position.

14. An anchoring system as in claim 7, wherein the front and back pairs of wall segments are disposed on the base member so as to be spaced from the at least two securement members.

15. An anchoring system as in claim 1 comprising a plurality of contact surfaces disposed so as to face the base member when the cover is in the engaged position.

16. An anchoring system as in claim 15, wherein the plurality of contact surfaces inhibits the catheter from being crushed between the base member and the cover.

17. An anchoring system as in claim 15, wherein the plurality of contact surfaces is disposed above the base member.

18. An anchoring system as in claim 1, wherein the cover is flexible.

19. An anchoring system as in claim 1, wherein each wall segment is disposed between the cover and the base member when the cover is in the engaged position.

20. An anchoring system as in claim 1, wherein the cover contacts at least the body of the fitting when the cover is in the engaged position.

21. An anchoring system as in claim 1, wherein the wall segments of each pair of wall segments inhibit lateral movement of the secured wing relative to the base member.

22. An anchoring system as in claim 7, wherein the at least two securement members are separate from the two pairs of wall segments.

23. An anchoring system as in claim 7, wherein each of the at least two securement members is configured as a latching arm.

24. A securement system for a catheter, the securement system comprising:
a fitting on a medical line, the fitting having a rigid body and a pair of outwardly extending wings;
a retainer having at least two upstanding members that are spaced apart to receive the rigid component therebetween and that cooperate so as to inhibit longitudinal movement of the medical article relative to the retainer;
a trough separate from the at least two upstanding members, the trough extending up from the retainer and positioned forward of the at least two upstanding members, the trough receiving at least a portion of the rigid body of the fitting;
a cover being movable between a first position and a second position, the cover being engaged with the retainer and covering at least part of the rigid body when in the second position; and
interengaging structure which releasably secures together the retainer and the cover in the second position.

25. A securement system as in claim 24 wherein the at least two upstanding members are disposed between the interengaging structure.

26. A securement system as in claim 25, wherein the interengaging structure is separate from the at least two upstanding members.

* * * * *